US012727994B1

(12) United States Patent
Levi et al.

(10) Patent No.: US 12,727,994 B1
(45) Date of Patent: Sep. 8, 2026

(54) PROSTHETIC HEART VALVE LEAFLET COMMISSURE ASSEMBLIES AND METHODS

(71) Applicant: Edwards Lifesciences Corporation, Irvine, CA (US)

(72) Inventors: Tamir S. Levi, Zikhron Yaakov (IL); Ziv Yohanan, Kfar Hahoresh (IL)

(73) Assignee: Edwards Lifesciences Corporation, Irvine, CA (US)

( * ) Notice: Subject to any disclaimer, the term of this patent is extended or adjusted under 35 U.S.C. 154(b) by 916 days.

(21) Appl. No.: 17/979,239

(22) Filed: Nov. 2, 2022

Related U.S. Application Data

(63) Continuation of application No. PCT/US2021/032381, filed on May 14, 2021.

(60) Provisional application No. 63/025,796, filed on May 15, 2020.

(51) Int. Cl.
*A61F 2/24* (2006.01)

(52) U.S. Cl.
CPC .... *A61F 2/2418* (2013.01); *A61F 2210/0057* (2013.01); *A61F 2220/0091* (2013.01)

(58) Field of Classification Search
CPC ............ A61F 2/2418; A61F 2210/0057; A61F 2220/0091
See application file for complete search history.

(56) References Cited

U.S. PATENT DOCUMENTS 3,409,013 A 11/1968 Berry
3,548,417 A 12/1970 Ronnie et al.
3,587,115 A 6/1971 Donald
3,657,744 A 4/1972 Ersek
3,671,979 A 6/1972 Moulopoulos
3,714,671 A 2/1973 Edwards et al.
3,755,823 A 9/1973 Hancock
4,035,849 A 7/1977 Angell et al.
(Continued)

FOREIGN PATENT DOCUMENTS

DE 0144167 C 9/1903
DE 2246526 A1 3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Suzette J Gherbi
(74) *Attorney, Agent, or Firm* — Klarquist Sparkman, LLP

(57) ABSTRACT

A prosthetic heart valve can comprise an annular frame and a leaflet assembly. The frame can be radially expandable and compressible between a radially compressed state and a radially expanded state. The leaflet assembly can comprise a plurality of leaflets coupled to each other to form commissures, which can be coupled to the frame using a plurality of commissure attachment members. The commissure attachment members can be mounted on respective commissure support portions for axial sliding movement between the commissure attachment members and the commissure support portions when the frame is radially compressed and expanded.

16 Claims, 9 Drawing Sheets

(56) References Cited

U.S. PATENT DOCUMENTS 4,056,854 A 11/1977 Boretos et al.
4,106,129 A 8/1978 Carpentier et al.
4,222,126 A 9/1980 Boretos et al.
4,265,694 A 5/1981 Boretos et al.
4,297,749 A 11/1981 Davis et al.
4,339,831 A 7/1982 Johnson
4,343,048 A 8/1982 Ross et al.
4,345,340 A 8/1982 Rosen
4,373,216 A 2/1983 Klawitter
4,406,022 A 9/1983 Roy
4,441,216 A 4/1984 Ionescu et al.
4,470,157 A 9/1984 Love
4,535,483 A 8/1985 Klawitter et al.
4,574,803 A 3/1986 Storz
4,592,340 A 6/1986 Boyles
4,605,407 A 8/1986 Black et al.
4,612,011 A 9/1986 Kautzky
4,643,732 A 2/1987 Pietsch et al.
4,655,771 A 4/1987 Wallsten
4,692,164 A 9/1987 Dzemeshkevich et al.
4,733,665 A 3/1988 Palmaz
4,759,758 A 7/1988 Gabbay
4,762,128 A 8/1988 Rosenbluth
4,777,951 A 10/1988 Cribier et al.
4,787,899 A 11/1988 Lazarus
4,787,901 A 11/1988 Baykut
4,796,629 A 1/1989 Grayzel
4,820,299 A 4/1989 Philippe et al.
4,829,990 A 5/1989 Thuroff et al.
4,851,001 A 7/1989 Taheri
4,856,516 A 8/1989 Hillstead
4,878,495 A 11/1989 Grayzel
4,878,906 A 11/1989 Lindemann et al.
4,883,458 A 11/1989 Shiber
4,922,905 A 5/1990 Strecker
4,966,604 A 10/1990 Reiss
4,979,939 A 12/1990 Shiber
4,986,830 A 1/1991 Owens et al.
4,994,077 A 2/1991 Dobben
5,007,896 A 4/1991 Shiber
5,026,366 A 6/1991 Leckrone
5,032,128 A 7/1991 Alonso
5,037,434 A 8/1991 Lane
5,047,041 A 9/1991 Samuels
5,059,177 A 10/1991 Towne et al.
5,080,668 A 1/1992 Bolz et al.
5,085,635 A 2/1992 Cragg
5,089,015 A 2/1992 Ross
5,152,771 A 10/1992 Sabbaghian et al.
5,163,953 A 11/1992 Vince
5,167,628 A 12/1992 Boyles
5,192,297 A 3/1993 Hull
5,266,073 A 11/1993 Wall
5,282,847 A 2/1994 Trescony et al.
5,295,958 A 3/1994 Shturman
5,332,402 A 7/1994 Teitelbaum
5,360,444 A 11/1994 Kusuhara
5,370,685 A 12/1994 Stevens
5,397,351 A 3/1995 Pavcnik et al.
5,411,055 A 5/1995 Kane
5,411,552 A 5/1995 Andersen et al.
5,443,446 A 8/1995 Shturman
5,480,424 A 1/1996 Cox
5,500,014 A 3/1996 Quijano et al.
5,545,209 A 8/1996 Roberts et al.
5,545,214 A 8/1996 Stevens
5,549,665 A 8/1996 Vesely et al.
5,554,185 A 9/1996 Block et al.
5,558,644 A 9/1996 Boyd et al.
5,571,175 A 11/1996 Vanney et al.
5,584,803 A 12/1996 Stevens et al.
5,591,185 A 1/1997 Kilmer et al.
5,591,195 A 1/1997 Taheri et al.
5,607,464 A 3/1997 Trescony et al.
5,609,626 A 3/1997 Quijano et al.
5,628,792 A 5/1997 Lentell
5,639,274 A 6/1997 Fischell et al.
5,665,115 A 9/1997 Cragg
5,716,417 A 2/1998 Girard et al.
5,728,068 A 3/1998 Leone et al.
5,749,890 A 5/1998 Shaknovich
5,756,476 A 5/1998 Epstein et al.
5,769,812 A 6/1998 Stevens et al.
5,800,508 A 9/1998 Goicoechea et al.
5,840,081 A 11/1998 Andersen et al.
5,855,597 A 1/1999 Jayaraman
5,855,601 A 1/1999 Bessler et al.
5,855,602 A 1/1999 Angell
5,925,063 A 7/1999 Khosravi
5,957,949 A 9/1999 Leonhardt et al.
6,027,525 A 2/2000 Suh et al.
6,132,473 A 10/2000 Williams et al.
6,168,614 B1 1/2001 Andersen et al.
6,171,335 B1 1/2001 Wheatley et al.
6,174,327 B1 1/2001 Mertens et al.
6,210,408 B1 4/2001 Chandrasekaran et al.
6,217,585 B1 4/2001 Houser et al.
6,221,091 B1 4/2001 Khosravi
6,231,602 B1 5/2001 Carpentier et al.
6,245,102 B1 6/2001 Jayaraman
6,299,637 B1 10/2001 Shaolian et al.
6,302,906 B1 10/2001 Goicoechea et al.
6,338,740 B1 1/2002 Carpentier
6,350,277 B1 2/2002 Kocur
6,352,547 B1 3/2002 Brown et al.
6,425,916 B1 7/2002 Garrison et al.
6,440,764 B1 8/2002 Focht et al.
6,454,799 B1 9/2002 Schreck
6,458,153 B1 10/2002 Bailey et al.
6,461,382 B1 10/2002 Cao
6,468,660 B2 10/2002 Ogle et al.
6,482,228 B1 11/2002 Norred
6,488,704 B1 12/2002 Connelly et al.
6,527,979 B2 3/2003 Constantz et al.
6,569,196 B1 5/2003 Vesely
6,582,462 B1 6/2003 Andersen et al.
6,605,112 B1 8/2003 Moll et al.
6,652,578 B2 11/2003 Bailey et al.
6,689,123 B2 2/2004 Pinchasik
6,716,244 B2 4/2004 Klaco
6,730,118 B2 5/2004 Spenser et al.
6,733,525 B2 5/2004 Yang et al.
6,767,362 B2 7/2004 Schreck
6,769,161 B2 8/2004 Brown et al.
6,783,542 B2 8/2004 Eidenschink
6,830,584 B1 12/2004 Seguin
6,878,162 B2 4/2005 Bales et al.
6,893,460 B2 5/2005 Spenser et al.
6,908,481 B2 6/2005 Cribier
6,936,067 B2 8/2005 Buchanan
7,018,406 B2 3/2006 Seguin et al.
7,018,408 B2 3/2006 Bailey et al.
7,096,554 B2 8/2006 Austin et al.
7,225,518 B2 6/2007 Eidenschink et al.
7,276,078 B2 10/2007 Spenser et al.
7,276,084 B2 10/2007 Yang et al.
7,316,710 B1 1/2008 Cheng et al.
7,318,278 B2 1/2008 Zhang et al.
7,374,571 B2 5/2008 Pease et al.
7,381,218 B2 * 6/2008 Schreck ................ A61F 2/2433 623/2.18
7,393,360 B2 7/2008 Spenser et al.
7,462,191 B2 12/2008 Spenser et al.
7,510,575 B2 3/2009 Spenser et al.
7,563,280 B2 7/2009 Anderson et al.
7,585,321 B2 9/2009 Cribier
7,618,446 B2 11/2009 Andersen et al.
7,618,447 B2 11/2009 Case et al.
7,655,034 B2 2/2010 Mitchell et al.
7,785,366 B2 8/2010 Maurer et al.
7,959,665 B2 6/2011 Pienknagura
7,959,672 B2 6/2011 Salahieh et al.
7,993,394 B2 8/2011 Hariton et al.
8,029,556 B2 10/2011 Rowe

(56) References Cited

U.S. PATENT DOCUMENTS 8,075,611 B2 12/2011 Millwee et al.
8,128,686 B2 3/2012 Paul et al.
8,167,932 B2 5/2012 Bourang et al.
8,291,570 B2 10/2012 Eidenschink et al.
8,348,998 B2 1/2013 Pintor et al.
8,449,606 B2 5/2013 Eliasen et al.
8,454,685 B2 6/2013 Hariton et al.
8,652,203 B2 2/2014 Quadri et al.
8,685,055 B2 4/2014 VanTassel et al.
8,747,463 B2 6/2014 Fogarty et al.
9,078,781 B2 7/2015 Ryan et al.
11,224,509 B2 1/2022 Dasi et al.
12,310,847 B2 * 5/2025 Dvorsky ................ A61F 2/243
12,343,253 B2 * 7/2025 Nir ........................ A61F 2/2418
2001/0021872 A1 9/2001 Bailey et al.
2002/0026094 A1 2/2002 Roth
2002/0032481 A1 3/2002 Gabbay
2002/0138135 A1 9/2002 Duerig et al.
2002/0143390 A1 10/2002 Ishii
2002/0173842 A1 11/2002 Buchanan
2003/0014105 A1 1/2003 Cao
2003/0040791 A1 2/2003 Oktay
2003/0050694 A1 3/2003 Yang et al.
2003/0100939 A1 5/2003 Yodfat et al.
2003/0158597 A1 8/2003 Quiachon et al.
2003/0212454 A1 11/2003 Scott et al.
2004/0024452 A1 2/2004 Kruse et al.
2004/0039436 A1 2/2004 Spenser et al.
2004/0078074 A1 4/2004 Anderson et al.
2004/0186558 A1 9/2004 Pavcnik et al.
2004/0186563 A1 9/2004 Lobbi
2004/0186565 A1 9/2004 Schreck
2004/0260389 A1 12/2004 Case et al.
2005/0010285 A1 1/2005 Lambrecht et al.
2005/0075725 A1 4/2005 Rowe
2005/0075728 A1 4/2005 Nguyen et al.
2005/0096736 A1 5/2005 Osse et al.
2005/0096738 A1 5/2005 Cali et al.
2005/0137686 A1 6/2005 Salahieh et al.
2005/0188525 A1 9/2005 Weber et al.
2005/0203614 A1 9/2005 Forster et al.
2005/0203617 A1 9/2005 Forster et al.
2005/0234546 A1 10/2005 Nugent et al.
2006/0004469 A1 1/2006 Sokel
2006/0025857 A1 2/2006 Bergheim et al.
2006/0058872 A1 3/2006 Salahieh et al.
2006/0074484 A1 4/2006 Huber
2006/0108090 A1 5/2006 Ederer et al.
2006/0149350 A1 7/2006 Patel et al.
2006/0183383 A1 8/2006 Asmus et al.
2006/0229719 A1 10/2006 Marquez et al.
2006/0259136 A1 11/2006 Nguyen et al.
2006/0259137 A1 11/2006 Artof et al.
2006/0287717 A1 12/2006 Rowe et al.
2007/0005131 A1 1/2007 Taylor
2007/0010876 A1 1/2007 Salahieh et al.
2007/0010877 A1 1/2007 Salahieh et al.
2007/0112422 A1 5/2007 Dehdashtian
2007/0162102 A1 7/2007 Ryan et al.
2007/0203503 A1 8/2007 Salahieh et al.
2007/0203575 A1 8/2007 Forster et al.
2007/0203576 A1 8/2007 Lee et al.
2007/0208550 A1 9/2007 Cao et al.
2007/0213813 A1 9/2007 Segesser et al.
2007/0233228 A1 10/2007 Eberhardt et al.
2007/0260305 A1 11/2007 Drews et al.
2007/0265700 A1 11/2007 Eliasen et al.
2008/0021546 A1 1/2008 Patz et al.
2008/0114442 A1 5/2008 Mitchell et al.
2008/0125853 A1 5/2008 Bailey et al.
2008/0154355 A1 6/2008 Benichou et al.
2008/0183271 A1 7/2008 Frawley et al.
2008/0208327 A1 8/2008 Rowe
2008/0243245 A1 10/2008 Thambar et al.
2008/0255660 A1 10/2008 Guyenot et al.
2008/0275537 A1 11/2008 Limon
2008/0294248 A1 11/2008 Yang et al.
2009/0118826 A1 5/2009 Khaghani
2009/0125118 A1 5/2009 Gong
2009/0157175 A1 6/2009 Benichou
2009/0276040 A1 11/2009 Rowe et al.
2009/0281619 A1 11/2009 Le et al.
2009/0287296 A1 11/2009 Manasse
2009/0287299 A1 11/2009 Tabor et al.
2009/0299452 A1 12/2009 Eidenschink et al.
2009/0319037 A1 12/2009 Rowe et al.
2010/0004735 A1 1/2010 Yang et al.
2010/0049313 A1 2/2010 Alon et al.
2010/0082094 A1 4/2010 Quadri et al.
2010/0100176 A1 4/2010 Elizondo et al.
2010/0168844 A1 7/2010 Toomes et al.
2010/0185277 A1 7/2010 Braido et al.
2010/0198347 A1 8/2010 Zakay et al.
2010/0204781 A1 8/2010 Alkhatib
2011/0015729 A1 1/2011 Jimenez et al.
2011/0022157 A1 1/2011 Essinger et al.
2011/0066224 A1 * 3/2011 White .................. A61F 2/2412
623/1.15
2011/0137397 A1 6/2011 Chau et al.
2011/0218619 A1 9/2011 Benichou et al.
2011/0319991 A1 12/2011 Hariton et al.
2012/0030090 A1 2/2012 Johnston et al.
2012/0089223 A1 4/2012 Nguyen et al.
2012/0101571 A1 4/2012 Thambar et al.
2012/0123529 A1 5/2012 Levi et al.
2012/0259409 A1 10/2012 Nguyen et al.
2013/0023985 A1 1/2013 Khairkhahan et al.
2013/0046373 A1 2/2013 Cartledge et al.
2013/0150956 A1 6/2013 Yohanan et al.
2013/0166017 A1 6/2013 Cartledge et al.
2013/0190857 A1 7/2013 Mitra et al.
2013/0274873 A1 10/2013 Delaloye et al.
2013/0310926 A1 11/2013 Hariton
2013/0317598 A1 11/2013 Rowe et al.
2013/0331929 A1 12/2013 Mitra et al.
2014/0194981 A1 7/2014 Menk et al.
2014/0200661 A1 7/2014 Pintor et al.
2014/0209238 A1 7/2014 Bonyuet et al.
2014/0222136 A1 8/2014 Geist et al.
2014/0277417 A1 9/2014 Schraut et al.
2014/0277419 A1 9/2014 Garde et al.
2014/0277424 A1 9/2014 Oslund
2014/0277563 A1 9/2014 White
2014/0296962 A1 * 10/2014 Cartledge ................ A61F 2/95
623/1.11
2014/0330372 A1 11/2014 Weston et al.
2014/0343670 A1 11/2014 Bakis et al.
2014/0343671 A1 11/2014 Yohanan et al.
2014/0350667 A1 11/2014 Braido et al.
2015/0073545 A1 3/2015 Braido
2015/0073546 A1 3/2015 Braido
2015/0135506 A1 * 5/2015 White .................. A61F 2/2415
29/428
2015/0157455 A1 6/2015 Hoang et al.
2016/0374802 A1 12/2016 Levi et al.
2017/0014229 A1 1/2017 Nguyen-Thien-Nhon et al.
2017/0360585 A1 * 12/2017 White ...................... A61F 2/86
2018/0028310 A1 2/2018 Gurovich et al.
2018/0153689 A1 6/2018 Maimon et al.
2018/0325665 A1 11/2018 Gurovich et al.
2018/0344456 A1 12/2018 Barash et al.
2019/0105153 A1 * 4/2019 Barash ................. A61F 2/2418
2019/0159894 A1 5/2019 Levi et al.
2019/0192288 A1 6/2019 Levi et al.
2019/0192289 A1 6/2019 Levi et al.
2021/0393398 A1 * 12/2021 Levi ....................... A61F 2/243

FOREIGN PATENT DOCUMENTS

DE 19532846 A1 3/1997
DE 19546692 A1 6/1997
DE 19857887 A1 7/2000
DE 19907646 A1 8/2000
DE 10049812 A1 4/2002

(56) References Cited

FOREIGN PATENT DOCUMENTS

| | | | |
|---|---|---|---|
| DE | 10049813 | C1 | 4/2002 |
| DE | 10049814 | A1 | 4/2002 |
| DE | 10049815 | A1 | 4/2002 |
| EP | 0103546 | B1 | 5/1988 |
| EP | 0850607 | A1 | 7/1998 |
| EP | 1057460 | A1 | 12/2000 |
| EP | 1088529 | A2 | 4/2001 |
| EP | 1570809 | A1 | 9/2005 |
| FR | 2788217 | A1 | 7/2000 |
| FR | 2815844 | A1 | 5/2002 |
| GB | 2056023 | A | 3/1981 |
| SU | 1271508 | A1 | 11/1986 |
| WO | 1991017720 | A1 | 11/1991 |
| WO | 1992017118 | A1 | 10/1992 |
| WO | 1993001768 | A1 | 2/1993 |
| WO | 1997024080 | A1 | 7/1997 |
| WO | 1998029057 | A1 | 7/1998 |
| WO | 1999030646 | A1 | 6/1999 |
| WO | 1999033414 | A1 | 7/1999 |
| WO | 1999040964 | A1 | 8/1999 |
| WO | 1999047075 | A1 | 9/1999 |
| WO | 2000018333 | A1 | 4/2000 |
| WO | 2000041652 | A1 | 7/2000 |
| WO | 2000047139 | A1 | 8/2000 |
| WO | 2001035878 | A2 | 5/2001 |
| WO | 2001049213 | A2 | 7/2001 |
| WO | 2001054624 | A1 | 8/2001 |
| WO | 2001054625 | A1 | 8/2001 |
| WO | 2001062189 | A1 | 8/2001 |
| WO | 2001064137 | A1 | 9/2001 |
| WO | 2001076510 | A2 | 10/2001 |
| WO | 2002022054 | A1 | 3/2002 |
| WO | 2002036048 | A1 | 5/2002 |
| WO | 2002041789 | A2 | 5/2002 |
| WO | 2002043620 | A1 | 6/2002 |
| WO | 2002047575 | A2 | 6/2002 |
| WO | 2002049540 | A2 | 6/2002 |
| WO | 2003047468 | A1 | 6/2003 |
| WO | 2005034812 | A1 | 4/2005 |
| WO | 2005055883 | A1 | 6/2005 |
| WO | 2005084595 | A1 | 9/2005 |
| WO | 2005102015 | A2 | 11/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A2 | 12/2006 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009094188 | A2 | 7/2009 |
| WO | 2009116041 | A2 | 9/2009 |
| WO | 2009149462 | A2 | 12/2009 |
| WO | 2010011699 | A2 | 1/2010 |
| WO | 2010121076 | A2 | 10/2010 |
| WO | 2013106585 | A1 | 7/2013 |
| WO | 2015085218 | A1 | 6/2015 |
| WO | WO-2024044177 | A1 * | 2/2024 ........... A61F 2/2418 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5): 1120-6. Epub Apr. 7, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al., "Prototype Stent: Invivo Swine Studies in the Biliary System", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

PROSTHETIC HEART VALVE LEAFLET COMMISSURE ASSEMBLIES AND METHODS

CROSS REFERENCE TO RELATED APPLICATION

The present application is a continuation of a PCT Application No. PCT/US2021/032381, entitled "PROSTHETIC HEART VALVE LEAFLET COMMISSURE ASSEMBLIES AND METHODS," filed May 14, 2021, which claims the benefit of U.S. Provisional Application No. 63/025,796, entitled "PROSTHETIC HEART VALVE LEAFLET COMMISSURE ASSEMBLIES AND METHODS," filed May 15, 2020, wherein each of the above-referenced is incorporated herein by reference.

FIELD

The present disclosure relates generally to prosthetic heart valves, and more particularly to methods and assemblies for forming commissures with leaflets of such prosthetic heart valves.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size.

Prosthetic valves that rely on a mechanical actuator for expansion can be referred to as "mechanically expandable" prosthetic heart valves. The actuator typically takes the form of pull cables, sutures, wires and/or shafts that are configured to transmit expansion forces from a handle of the delivery apparatus to the prosthetic valve.

Most expandable, transcatheter heart valves comprise a cylindrical metal frame or stent and prosthetic leaflets mounted inside the frame. The leaflets may be attached to the frame at commissure tabs (also referred to as leaflet tabs) of the leaflets. For example, a commissure may be formed by connecting the commissure tabs of two adjacent leaflets to one another, and in some embodiments, to an attachment element configured to couple to a commissure support portion of the frame. The commissure or the attachment element can then be attached to the commissure support portion of the frame via a fastener, such as a suture.

Typical commissures or commissure assemblies can be relatively complex and time consuming to form and suture to the commissure support portion of the frame, in part due to the numerous stitches that can be required. Further, these types of commissures and attachment methods to the commissure support portion can be subject to wear along the numerous stitches, as well as along portions of the commissure tabs that wrap around a side and/or outer-facing surface of the commissure support portion.

Frames of prosthetic heart valves, in general, are foreshortened when radially expanded and therefore the leaflets undergo changes during the crimping and expansion of the frame of the valve. For example, the upper and lower edges of a commissure typically are fixed to the frame or a commissure support portion. Radial compression of the frame causes the upper and lower attachment locations to move closer to each other, while radial expansion of the frame causes the upper and lower attachment locations to move further apart from each other. As such, the height of the commissure from the lower edge to the upper edge must be great enough to extend the distance between the attachment locations when the frame is radially compressed. However, this can result in undesirable slack to form in the commissure when the frame is radially expanded.

Accordingly, a need exists for improved prosthetic heart valve leaflet assemblies, and commissures formed with such leaflet assemblies, and methods for assembling commissures to a frame of a prosthetic heart valve.

SUMMARY

Described herein are embodiments of prosthetic heart valves and method for assembling prosthetic heart valves including an annular frame and leaflet assembly. The frame can be radially expandable and compressible between a radially compressed state and a radially expanded state. The leaflet assembly can comprise a plurality of leaflets coupled to each other to form commissures, which can be coupled to the frame using a plurality of commissure attachment members. The commissure attachment members can be mounted on respective commissure support portions for axial sliding movement between the commissure attachment members and the commissure support portions when the frame is radially compressed and expanded. This allows the commissures to maintain a constant height without any axial deformation during radial compression and expansion of the frame.

In one representative embodiment, a prosthetic heart valve comprises an annular frame comprising a plurality of interconnected struts, wherein the frame is radially compressible and expandable between a radially compressed state and a radially expanded state, wherein the frame comprises a plurality of commissure support portions; a plurality of leaflets situated within the frame, each leaflet comprising a body and two opposing commissure tabs arranged on opposite sides of the body; and a plurality of commissure attachment elements, wherein each commissure tab of a leaflet is paired with an adjacent commissure tab of an adjacent leaflet and the pair of commissure tabs are connected to one of the commissure attachment elements to form a plurality of commissures; wherein each commissure attachment element is slidably mounted on one of the commissure support portions such that the commissures can slide axially relative to the commissure support portions when the frame is radially expanded and compressed between the radially compressed state and the radially expanded state.

In another representative embodiment, a prosthetic heart valve comprises an annular frame comprising a plurality of first struts overlapping and pivotably connected to a plurality of second struts at a plurality of pivot joints, wherein the frame is radially compressible and expandable between a radially compressed state and a radially expanded state; wherein the frame comprises a plurality of actuators, each comprising first and second members that are axially moveable relative to each other to produce radial expansion and compression of the frame; a plurality of leaflets situated within the frame, each leaflet comprising a body and two opposing commissure tabs arranged on opposite sides of the body; and a plurality of commissure attachment elements, wherein each commissure tab of a leaflet is paired with an adjacent commissure tab of an adjacent leaflet and the pair of commissure tabs are connected to one of the commissure attachment elements to form a plurality of commissures; wherein each commissure attachment element is slidably mounted on the first member of one of the actuators such that the commissures can slide axially relative to the first members when the frame is radially expanded and compressed between the radially compressed state and the radially expanded state.

In another representative embodiment, a prosthetic heart valve comprises an annular frame comprising a plurality struts, wherein the frame is radially compressible and expandable between a radially compressed state and a radially expanded state; wherein the frame comprises a plurality of actuators, each comprising first and second members that are axially moveable relative to each other to produce radial expansion and compression of the frame; a plurality of leaflets situated within the frame, each leaflet comprising a body having a cusp edge portion and two opposing commissure tabs arranged on opposite sides of the body; and a plurality of commissure attachment elements, wherein each commissure tab of a leaflet is paired with an adjacent commissure tab of an adjacent leaflet and the pair of commissure tabs are connected to one of the commissure attachment elements to form a plurality of commissures; wherein each commissure attachment element is slidably mounted on the first member of one of the actuators such that the commissures can slide axially relative to the first members when the frame is radially expanded and compressed between the radially compressed state and the radially expanded state.

In another representative embodiment, a prosthetic heart valve comprises an annular frame comprising a plurality of first struts overlapping and pivotably connected to a plurality of second struts at a plurality of pivot joints, wherein the frame is radially compressible and expandable between a radially compressed state and a radially expanded state; a plurality of leaflets situated within the frame, each leaflet comprising a body and two opposing commissure tabs arranged on opposite sides of the body; and a plurality of commissure attachment elements, wherein each commissure tab of a leaflet is paired with an adjacent commissure tab of an adjacent leaflet and the pair of commissure tabs are connected to one of the commissure attachment elements to form a plurality of commissures; wherein each commissure attachment element is connected to one of the pivot joints such that the commissure attachment element is retained axially by the pivot joint when the frame is radially expanded and compressed between the radially compressed state and the radially expanded state.

In another representative embodiment, a method of assembling a prosthetic heart valve comprising a frame and a plurality of leaflets is provided. The frame is radially compressible and expandable between a radially compressed state and a radially expanded state. The method comprises forming a plurality of commissures with the plurality of leaflets, each leaflet including two opposing commissure tabs arranged on opposite sides of a body of the leaflet, wherein each commissure is formed by pairing each commissure tab of each leaflet with an adjacent commissure tab of an adjacent leaflet and coupling each pair of commissure tabs to a commissure attachment member; and mounting each commissure attachment member on a commissure support portion of the frame such that the commissures and the commissure support portions can slide axially relative to each other when the frame moves from the radially compressed state and the radially expanded state, and vice versa.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the invention will become more apparent from the following detailed description, which proceeds with reference to the accompanying figures.

DETAILED DESCRIPTION

General Considerations

Figure 1:
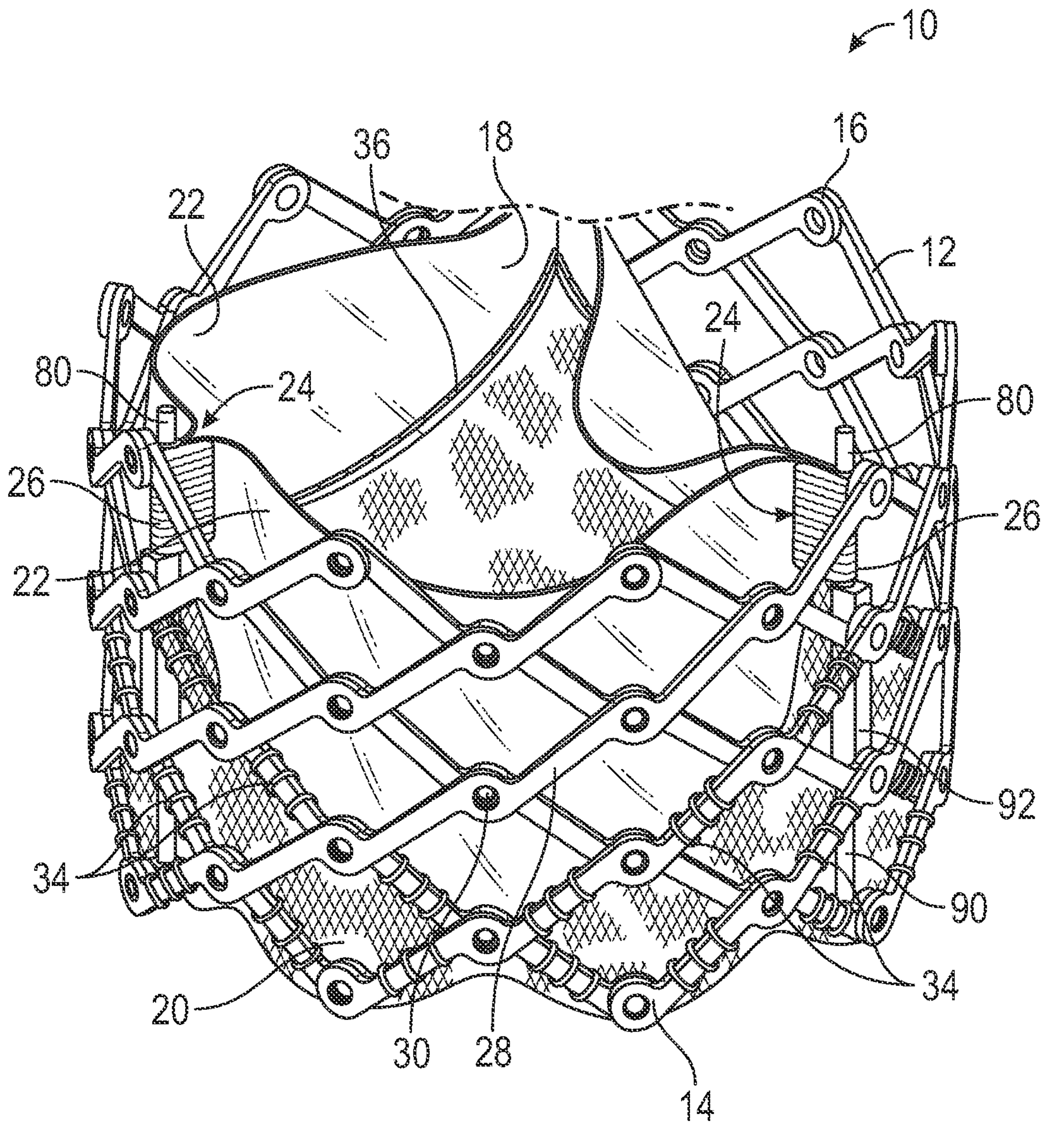
FIG. 1 is a perspective view of an example of a prosthetic heart valve.

For purposes of this description, certain aspects, advantages, and novel features of examples of this disclosure are described herein. The disclosed methods, apparatus, and systems should not be construed as being limiting in any way. Instead, the present disclosure is directed toward all novel and nonobvious features and aspects of the various disclosed examples, alone and in various combinations and sub-combinations with one another. The methods, apparatus, and systems are not limited to any specific aspect or feature or combination thereof, nor do the disclosed examples require that any one or more specific advantages be present or problems be solved.

Although the operations of some of the disclosed examples are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

Prosthetic valves disclosed herein can be radially compressible and expandable between a radially compressed state and a radially expanded state. Thus, the prosthetic valves can be crimped on or retained by an implant delivery apparatus in the radially compressed state during delivery, and then expanded to the radially expanded state once the prosthetic valve reaches the implantation site. It is understood that the prosthetic valves disclosed herein may be used with a variety of implant delivery apparatuses and can be implanted via various delivery procedures, examples of which will be discussed in more detail later.

FIG. 1 shows an exemplary prosthetic heart valve 10, according to one example. The prosthetic heart valve 10 can be radially compressible and expandable between a radially compressed configuration for delivery into a patient and a radially expanded configuration.

Any of the prosthetic valves disclosed herein are adapted to be implanted in the native aortic annulus, although in other examples they can be adapted to be implanted in the other native annuluses of the heart (the pulmonary, mitral, and tricuspid valves). The disclosed prosthetic valves also can be implanted within vessels communicating with the heart, including a pulmonary artery (for replacing the function of a diseased pulmonary valve, or the superior vena cava or the inferior vena cava (for replacing the function of a diseased tricuspid valve) or various other veins, arteries and vessels of a patient. The disclosed prosthetic valves also can be implanted within a previously implanted prosthetic valve (which can be a prosthetic surgical valve or a prosthetic transcatheter heart valve) in a valve-in-valve procedure.

In some examples, the disclosed prosthetic valves can be implanted within a docking or anchoring device that is implanted within a native heart valve or a vessel. For example, in one example, the disclosed prosthetic valves can be implanted within a docking device implanted within the pulmonary artery for replacing the function of a diseased pulmonary valve, such as disclosed in U.S. Publication No. 2017/0231756, which is incorporated by reference herein. In another example, the disclosed prosthetic valves can be implanted within a docking device implanted within or at the native mitral valve, such as disclosed in PCT Publication No. WO2020/247907, which is incorporated herein by reference. In another example, the disclosed prosthetic valves can be implanted within a docking device implanted within the superior or inferior vena cava for replacing the function of a diseased tricuspid valve, such as disclosed in U.S. Publication No. 2019/0000615, which is incorporated herein by reference.

The prosthetic heart valve 10 can include an annular stent or frame 12 having a first end 14 and a second end 16. In the depicted embodiment, the first end 14 is an inflow end and the second end 16 is an outflow end. The outflow end 16 can be coupled to a delivery apparatus for delivering and implanting the prosthetic heart valve within the native aortic valve is a transfemoral, retrograde delivery approach. Thus, in the delivery configuration of the prosthetic heart valve, the outflow end 16 is the proximal-most end of the prosthetic valve. In other embodiments, the inflow end 14 can be coupled to the delivery apparatus, depending on the particular native valve being replaced and the delivery technique that is used (e.g., trans-septal, transapical, etc.). For example, the inflow end 14 can be coupled to the delivery apparatus (and therefore is the proximal-most end of the prosthetic heart valve in the delivery configuration) when delivering the prosthetic heart valve to the native mitral valve via a trans-septal delivery approach.

The frame 12 can be made of any of various suitable materials, such as stainless steel, a cobalt chromium alloy, or a nickel titanium alloy ("NiTi"), for example Nitinol. Referring again to FIG. 1, as shown, the frame 12 can include a plurality of interconnected struts 28 arranged in a lattice-type pattern. The struts 28 are shown as positioned diagonally, or offset at an angle relative to, and radially offset from, a longitudinal axis of the prosthetic heart valve 10 when the prosthetic heart valve 10 is in the expanded configuration. In other implementations, the struts 28 can be offset by a different amount than depicted in FIG. 1, or some or all of the struts 28 can be positioned parallel to the longitudinal axis of the prosthetic heart valve 10.

In the illustrated embodiment, the struts 28 are pivotably coupled to one another at one or more pivot joints along the length of each strut. For example, in the illustrated configuration, each of the struts 28 can be formed with apertures at opposing ends of the strut and apertures spaced along the length of the strut. Respective hinges can be formed at the locations where struts 28 overlap each other via fasteners or pivot members, such as rivets or pins 30 that extend through the apertures. The hinges can allow the struts 28 to pivot relative to one another as the frame 12 is radially expanded or compressed, such as during assembly, preparation, or implantation of the prosthetic heart valve 10. In some embodiments, a pivot joint can comprise a rivet or pin 30 that extends through apertures of an inner strut and an outer strut that overlaps the inner strut at the pivot joint. In other embodiments, a pivot joint can comprise a rivet or pin 30 that is integrally formed on one of the inner or outer struts and extends through an aperture in the other one of the inner and outer strut.

Figures 2A, 2B:
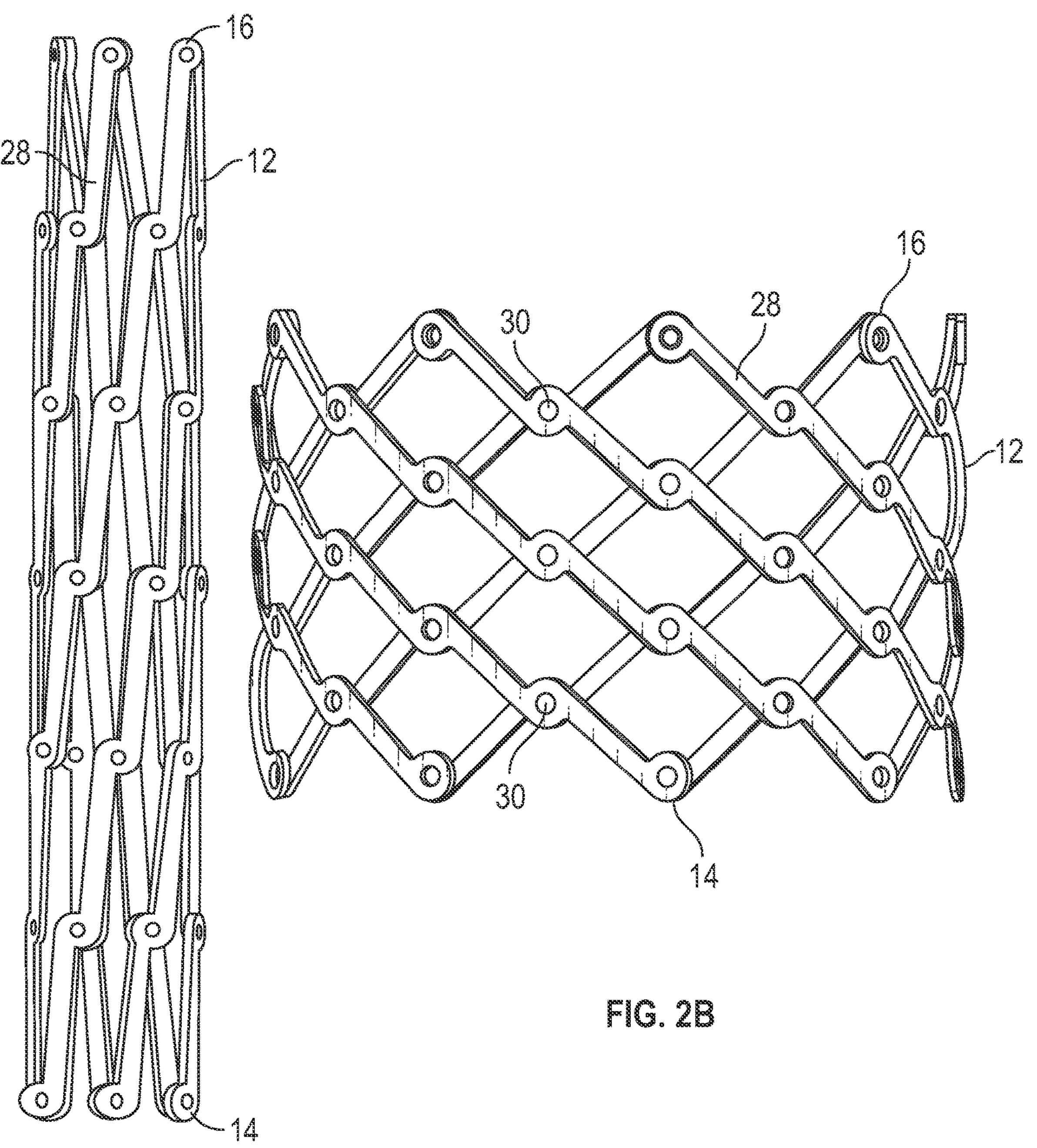
FIG. 2A is a side view of the frame of the prosthetic valve of FIG. 1 shown in a radially compressed state.
FIG. 2B is a side view of the frame of the prosthetic valve of FIG. 1 shown in a radially expanded state.

FIG. 2A shows the frame 12 of the prosthetic valve in a radially compressed state and FIG. 2B shows the frame of the prosthetic valve in a radially expanded state. As shown, when radially compressed, the frame 12 elongates axially, and when radially expanded, the frame 12 foreshortens.

In some embodiments, the frame 12 can be constructed by forming individual components (e.g., the struts and fasteners of the frame) and then mechanically assembling and connecting the individual components together. Further details regarding the construction of the frame and the prosthetic heart valve are described in U.S. Patent Application Publication Nos. 2018/0153689, 2018/0344456, 2019/0060057, and 2019/0105153, U.S. patent application Ser. No. 16/788,090, filed Feb. 11, 2020, and 62/945,000, filed Dec. 6, 2019, and PCT Application No. PCT/US2020/063205, filed Dec. 4, 2020, all of which are incorporated herein by reference.

In other embodiments, the struts 28 are not coupled to each other with respective hinges but are otherwise pivotable or bendable relative to each other to permit radial expansion and contraction of the frame 12. For example, the frame 12 can be formed (e.g., via laser cutting, electroforming or physical vapor deposition) from a single piece of material (e.g., a metal tube). Examples of such frames are disclosed in U.S. Pat. No. 9,393,110 and U.S. Publication No. 2018/0028310, which are incorporated herein by reference.

The prosthetic heart valve 10 can also include a valvular structure 18 which is coupled to the frame 12 and configured to regulate the flow of blood through the prosthetic heart valve 10 from the inflow end 14 to the outflow end 16. The prosthetic heart valve 10 can further include a plurality of actuators 80 mounted to and equally spaced around the inner surface of the frame 12. The actuators are configured to apply expansion and compression to the frame for radially expanding and compressing the prosthetic valve.

In the illustrated embodiment, the actuators 80 are linear actuators, each of which comprises an inner member, or piston, 90 and an outer member, or cylinder, 92. The inner member 90 is pivotably coupled to a junction of the frame, such as at the first end 14, while the outer member 92 is pivotably coupled to another junction of the frame closer to the second end 16. Moving the inner member 90 proximally relative to the outer member 92 and/or moving the outer member 92 distally relative to the inner member 90 is effective to radially expand the prosthetic valve. Conversely, moving the inner member 90 distally relative to the outer member 92 and/or moving the outer member 92 proximally relative to the inner member 90 is effective to radially compress the prosthetic valve. The actuators 80 can include locking mechanisms that are configured to retain the prosthetic valve in an expanded state inside the patient's body.

In some embodiments, each of the actuators 80 can be configured to form a releasable connection with one or more respective actuators of a delivery apparatus of a transcatheter delivery system. The actuators of the delivery apparatus can transmit forces from a handle of the delivery apparatus to the actuators 80 for expanding or compressing the prosthetic valve. Further details of the actuators, locking mechanisms and delivery apparatuses for actuating the actuators can be found in U.S. Patent Application Publication Nos. 2018/0153689, 2019/0060057 and 2018/0325665, U.S. Application No. 62/990,299, filed Mar. 16, 2020, and PCT Application No. PCT/US2021/022467, filed Mar. 16, 2021, each of which is incorporated herein by reference in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

In some embodiments, each of the actuators 80 can be used to support a respective commissure 24 (described below). As such, the actuators 80 can include commissure support portions for supporting and attaching commissures 24 of the valvular structure 18 to the frame 12, as described further herein.

The valvular structure 18 can include, for example, a leaflet assembly comprising one or more leaflets 22 (three leaflets 22 in the illustrated embodiment) made of a flexible material. The leaflets 22 of the leaflet assembly can be made from in whole or part, biological material, bio-compatible synthetic materials, or other such materials. Suitable biological material can include, for example, bovine pericardium (or pericardium from other sources). Each leaflet 22 includes two opposing commissure tabs arranged on opposite sides of a body of the leaflet. The body of the leaflet may be the portion of the leaflet that is adapted to bend and move during operation of the prosthetic heart valve 10. The commissure tabs of adjacent leaflets 22 can be arranged to form commissures 24, which can be, for example, mounted to commissure support portions of respective actuators 80.

Further details regarding transcatheter prosthetic heart valves, including the manner in which the valvular structure can be mounted to the frame of the prosthetic valve can be found, for example, in U.S. Pat. Nos. 6,730,118, 7,393,360, 7,510,575, 7,993,394, and 8,252,202, U.S. Publication Nos. 2018/0325665, 2019/0105153, and 2019/0192296, U.S. Patent Application Nos. 62/797,837, filed Jan. 28, 2019, 62/823,905, filed Mar. 26, 2019, 62/854,702, filed May 30, 2019, 62/928,993, filed Oct. 31, 2019, 62/959,723, filed Jan. 10, 2020, 62/971,011, filed Feb. 6, 2020, 62/985,558, filed Mar. 5, 2020, and 62/960,838, filed Jan. 14, 2020, and PCT Application Nos. PCT/US2019/61392, filed Nov. 14, 2019, PCT/US2020/18664, filed Feb. 18, 2020, PCT/US2020/014701, filed Jan. 23, 2020, PCT/US2020/057527, filed Oct. 27, 2020, PCT/US2020/024559, filed Mar. 25, 2020, PCT/US2021/012146, filed Jan. 5, 2021, PCT/US2021/012686, filed Jan. 8, 2021, PCT/US2021/016511, filed Feb. 4, 2021, and PCT/US2021/020206, filed Mar. 1, 2021, all of which are incorporated herein by reference in their entireties.

In some embodiments, as shown in FIG. 1, the commissures 24 can be mounted (e.g., sutured) directly to commissure support portions of the actuators 80 of the frame 12 via commissure attachment elements 26, which can be a piece of cloth or fabric. As one example, the commissure attachment elements 26 may include one or more stitches securing the commissures 24 to corresponding actuators 80. In other embodiments, the commissures 24 can be mounted to support struts or posts of the frame that are separate from the actuators 80. In still other embodiments, the commissures may be secured to an additional commissure attachment or support member (as described further herein) and the support member is then secured to a commissure support portion of an actuator 80 or support struts or posts of the frame.

The prosthetic heart valve 10 can also include one or more skirts or sealing members. For example, as shown in FIG. 1, the prosthetic heart valve 10 can include an inner skirt 20 mounted on the inner surface of the frame 12. As shown in FIG. 1, the inner skirt 20 is a circumferential inner skirt that spans an entire circumference of the inner surface of the frame 12. The inner skirt 20 can function as a sealing member to prevent or decrease perivalvular leakage (e.g., when the valve is placed at the implantation site) and as an attachment surface to anchor the leaflets 22 to the frame 12. For example, the inflow (e.g., cusp) edges of the leaflets 22 can be sutured directly to the inner skirt 20 along a stitching line 36 (which can be referred to as a "scallop line"). The inner skirt 20 in turn can be directly connected to selected struts 28 of the frame, such as with sutures 34, as shown in FIG. 1.

The prosthetic heart valve 10 can also include an outer skirt mounted on the outer surface of the frame 12 (not shown in FIG. 1). The outer skirt can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials (e.g., PET) or natural tissue (e.g., pericardial tissue). The inner and outer skirts can be mounted to the frame using sutures, an adhesive, welding, and/or other means for attaching the skirts to the frame.

Figure 3:
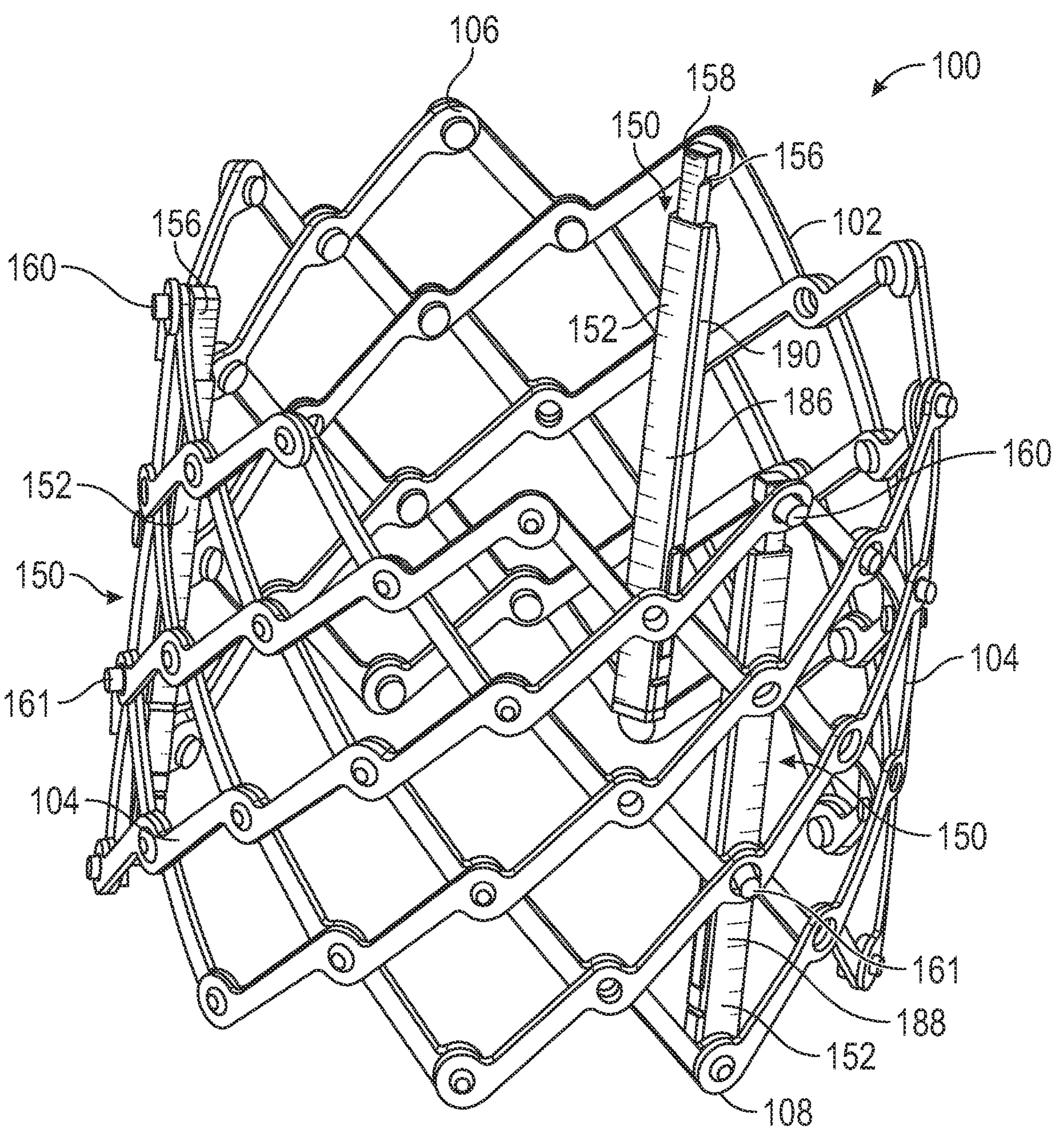
FIG. 3 is a perspective view of a prosthetic heart valve comprising three expansion and locking mechanisms, according to another example.
Figure 4:
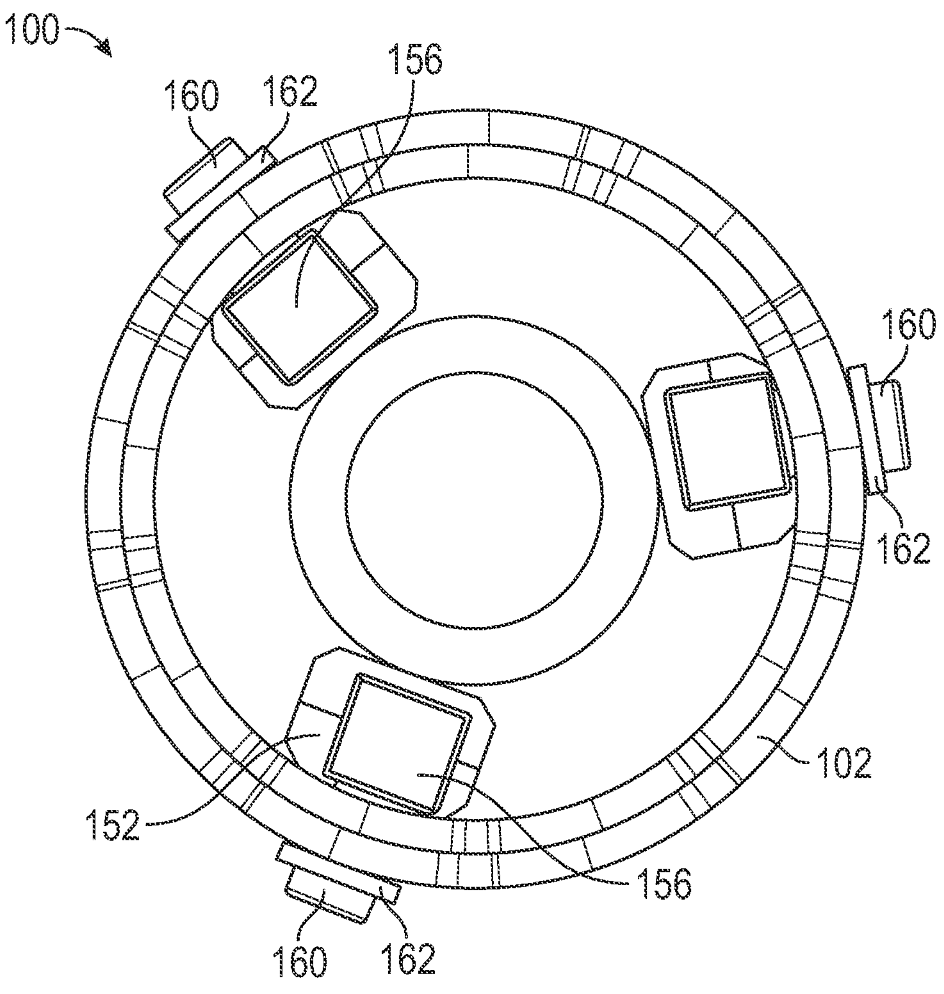
FIG. 4 is a top view of the prosthetic heart valve of FIG. 3 shown in a radially collapsed state.

FIGS. 3 and 4 illustrate an exemplary embodiment of a prosthetic valve 100, according to another embodiment, the prosthetic valve 100 comprising a frame 102 and one or more expansion and locking mechanisms 150 (also referred to as actuators). The frame 102 comprises a plurality of pivotably connected struts 104 defining an inflow end 106 (which is the distal end of the frame in a delivery configuration for the illustrated embodiment) and an outflow end 108 (which is the proximal end of the frame in the delivery configuration for the illustrated embodiment). The struts 104 are pivotably connected to each other at a plurality of junctions that permit pivoting of the struts relative to each other when the frame 102 is radially compressed and expanded, as described above in connection with prosthetic valve 10.

The prosthetic valve 100 can include a valvular structure (e.g., valvular structure 18) and inner and/or outer skirts, as previously described, although these components are omitted from FIGS. 3 and 4 for purposes of illustration. The one or more expansion and locking mechanisms 150 can be used in lieu of or in addition to actuators 80 described above. The expansion and locking mechanisms 150 can be used to both radially expand and lock the frame 102 of prosthetic valve 100 in a radially expanded state. In some embodiments, the commissures of the leaflets may be attached to a commissure support portion of the expansion and locking mechanisms 150. In alternate embodiments, the commissures of the leaflets may be attached to additional commissure posts of the frame 102.

FIG. 3 shows three expansion and locking mechanisms 150 mounted to the frame 102 with the frame 102 shown in the radially expanded configuration. Though the illustrated embodiment shows three expansion and locking mechanisms 150 spaced apart from each other about the circumference of the frame, it should be noted that a prosthetic valve can comprise any number of expansion and locking mechanisms 150. For example, in some embodiments, a prosthetic valve can comprise a single expansion and locking mechanism, or two expansion and locking mechanisms, or four expansion and locking mechanisms, etc. The expansion and locking mechanisms 150 can be placed at any position about the circumference of the frame 102. For example, in some embodiments, such as the illustrated embodiment, the expansion and locking mechanisms 150 are equally spaced from one another about the circumference of the frame 102. In other embodiments, it can be advantageous to have two or more expansion and locking mechanisms situated adjacent to one another.

Each expansion and locking mechanism 150 can include an outer member in the form of a sleeve 152 having an inner lumen, cavity, or bore and an inner member 156 extending at least partially into the cavity. The sleeve 152 in the illustrated embodiment comprises an inner wall 186, an outer wall 188, and two side walls 190, each of which extends radially between a longitudinal edge of the inner wall 186 and an opposing longitudinal edge of the outer wall 188. The inner wall 186, the outer wall 188, and the two side walls 190 define the cavity, which is sized and shaped to receive the inner member 156.

The sleeve 152 in the illustrated embodiment has a rectangular shape in cross-section and the inner member 156 has a rectangular shape in cross-section corresponding to the shape of the bore. In other embodiments, the sleeve 152 and/or the inner member 156 can have a square cross-sectional profile. As shown in FIG. 3, the rectangular and/or square cross-sections can advantageously minimize the distance that the expansion and locking members extend into the lumen of the frame 102, which can reduce the overall crimp profile of the valve 100. However, in other embodiments, the sleeve and the inner member can have any of various corresponding shapes in cross-section, for example, circular, ovular, triangular, rectangular, square, or combinations thereof.

As best shown in FIG. 3, a distal end portion 158 of the inner member 156 can be coupled to the frame 102 at a first location via a fastener 160 that is affixed to and extends radially from the distal end portion 158 of the inner member 156. The fastener 160 can be for example, a rivet or pin. As shown, in some embodiments, the fastener 160 can extend through corresponding apertures at a junction of two overlapping struts 104 of the frame 102 and can serve as a pivot pin around which the two struts 104 can pivot relative to each other and the inner member 156. In some embodiments, an end cap or nut 162 (as shown in FIG. 4) can be disposed over an end portion of the fastener 160. The nut 162 can have a diameter greater than the diameter of the apertures to retain the fastener 160 within the apertures. In alternative embodiments, the inner member 156 need not comprise a fastener 160 and can be coupled to the frame 102 via other means of attachment such as welding, adhesives, etc.

The sleeve 152 can be coupled to the frame 102 at a second location, axially spaced from the first location. For example, in the illustrated embodiment, the inner member 156 is secured to the frame 102 near the distal or inflow end 106 of the frame and the sleeve 152 is secured to the frame 102 closer to or at the proximal or outflow end 108 of the frame, such as via a fastener 161 (e.g., a rivet or pint). The fastener 161 is affixed to and extends radially from the sleeve 152 through corresponding apertures at a junction of two overlapping struts 104 and can serve as a pivot pin around which the two struts 104 can pivot relative to each other and the sleeve 152. A nut 162 can be mounted on each fastener 161 to retain the fastener within the corresponding apertures. The expansion and locking mechanism 150 can be pivotably coupled to the frame 102 at any two axially spaced, circumferentially aligned locations on the frame.

The inner member 156 can be axially movable relative to the sleeve 152 in a proximal direction and in a distal direction, along a central longitudinal axis of the frame 102. As such, because the inner member 156 and the sleeve 152 are secured to the frame at axially spaced locations, moving the inner member 156 and the sleeve 152 axially with respect to one another in a telescoping manner can cause radial expansion or compression of the frame 102. For example, moving the inner member 156 proximally toward the outflow end 108 of the frame, while holding the sleeve 152 in a fixed position and/or moving the sleeve 152 distally toward the inflow end 106 of the frame can cause the frame 102 to foreshorten axially and expand radially. Conversely, moving the inner member 156 distally and/or moving the sleeve 152 proximally causes the frame 102 to elongate axially and compress radially.

A prosthetic valve 100 including one or more expansion and locking mechanisms 150 can be expanded in the following exemplary manner. Generally, the prosthetic valve 100 is placed in a radially compressed state and releasably coupled to a distal end portion of a delivery apparatus, and then advanced through the vasculature of a patient to a selected implantation site (e.g., the native aortic annulus). The prosthetic valve 100 can then be deployed at the implantation site and expanded and locked in the expanded configuration using the expansion and locking mechanisms 150. Further details regarding the prosthetic valve, the expansion and locking mechanisms, and delivery apparatuses for actuating the expansion and locking mechanism can be found in U.S. Provisional Application Nos. 62/928,291, 62/950,005, and 62/981,666, the contents of which are incorporated herein by reference.

Figure 5:
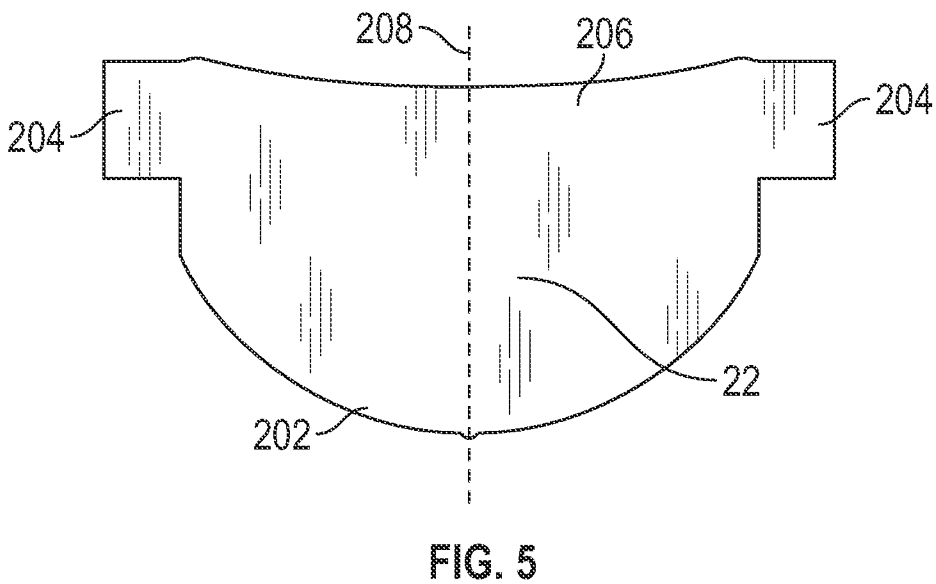
FIG. 5 is a plan view of one of the leaflets of the prosthetic valve of FIG. 1.

FIG. 5 shows a plan view of one of the leaflet 22 of prosthetic valve 10. A plurality of such leaflets 22 also can be implemented in the prosthetic valve 100 or any of the prosthetic valves disclosed herein. As shown in FIG. 5, each leaflet 22 can comprise a main, cusp edge portion 202 (also referred to as the inflow edge portion of the leaflet), two leaflet tabs 204 (also referred to as commissure tabs) at opposing ends of the cusp edge portion 202, and an upper edge portion 206 (also referred to as the outflow edge portion or the coaptation edge portion of the leaflet).

At each end of the cusp edge portion 202, a lower commissure portion 210 (also referred to as a transition section) extends between the adjacent upper end of the cusp end portion and the adjacent lower end of a leaflet tab 204. In the illustrated embodiment, the lower commissure portions 210 form straight, vertical edges of the leaflets. However, in other embodiments, the edges of the lower commissure portions 210 can have other shapes, for example, they can form additional leaflet tabs that may be axially spaced from the adjacent tabs 204. In still other embodiments, the upper ends of the cusp edge portion 202 can intersect the commissure tabs 204.

The cusp edge portion 202, leaflet tabs 204, the lower commissure portions 210, and upper edge portion 206 may be arranged around an outer perimeter of the leaflet 22, with the upper edge portion 206 extending between the two leaflet tabs 204 at an upper edge of the leaflet 22 and the cusp edge portion 202 extending between the two leaflet tabs 204 at a lower edge of the leaflet 22. As used here, “upper” and “lower” may be relative to a central longitudinal axis of the prosthetic heart valve 10 when the leaflet assembly is installed and coupled to frame 12 of the prosthetic heart valve 10.

In some embodiments, the cusp edge portion 202 has a curved, scalloped shape (as shown in FIG. 5). Thus, the cusp edge portion 202 may curve between the two leaflet tabs 204. FIG. 5 further illustrates a centerline 208 for each of the individual leaflets 22, which may also be a centerline of the leaflet assembly. For example, when assembled, the centerlines 208 for each of the leaflets 22 may overlap. Further, as shown in FIG. 5, the leaflet tabs 204 may be arranged at opposing ends of the lower commissure portions 210, across the centerline 208 from one another. In some embodiments, the leaflets and/or components of the leaflet assembly may have symmetry with respect to the centerline 208.

Other leaflet configurations that may be implemented in any of the prosthetic valves disclosed herein are described in U.S. Publication No. 2018/0028310, U.S. Application No. 62/978,455, filed Feb. 19, 2020, and PCT Application No. PCT/US2021/017336, filed Feb. 10, 2021, which are incorporated herein by reference.

Each commissure tab 204 can be paired with a commissure tab 204 of an adjacent leaflet and connected to each other and/or an attachment member 26 (FIG. 1), which can be mounted to upper portions of actuators 80, as depicted in FIG. 1. The adjacent lower commissure portions 210 of adjacent leaflets 22 can be connected to each other sutures. The cusp edge portions 202 of the leaflets 22 can be sutured to the inner skirt 20, which in turn can be connected to selected struts of the frame with sutures 34. In this manner, the lower-most edge of a commissure 24 (where the lower commissure portion 210 intersects the cusp edge portion 202) is fixed relative to the frame at a location that moves axially relative to the location where upper-most edge of the commissure 24 is fixed relative to the actuator 80 when the frame is radially expanded and compressed. Thus, when the frame is radially expanded, these attachment locations move closer together and can create slack or a “belly” along the stitching line(s) that secures a pair of commissure tabs 204 and/or lower commissure portions 210 together to form the commissure.

Thus, in particular embodiments, a prosthetic valve comprises a plurality of leaflets arranged to form a plurality of commissures that are slidably mounted on respective commissure supports for allowing the commissure supports to move axially relative to the commissures. In this manner, the commissures can maintain fixed positions relative to the upper ends of the cusp edge portions of the leaflets when the frame is radially compressed and expanded.

Figures 6, 7:
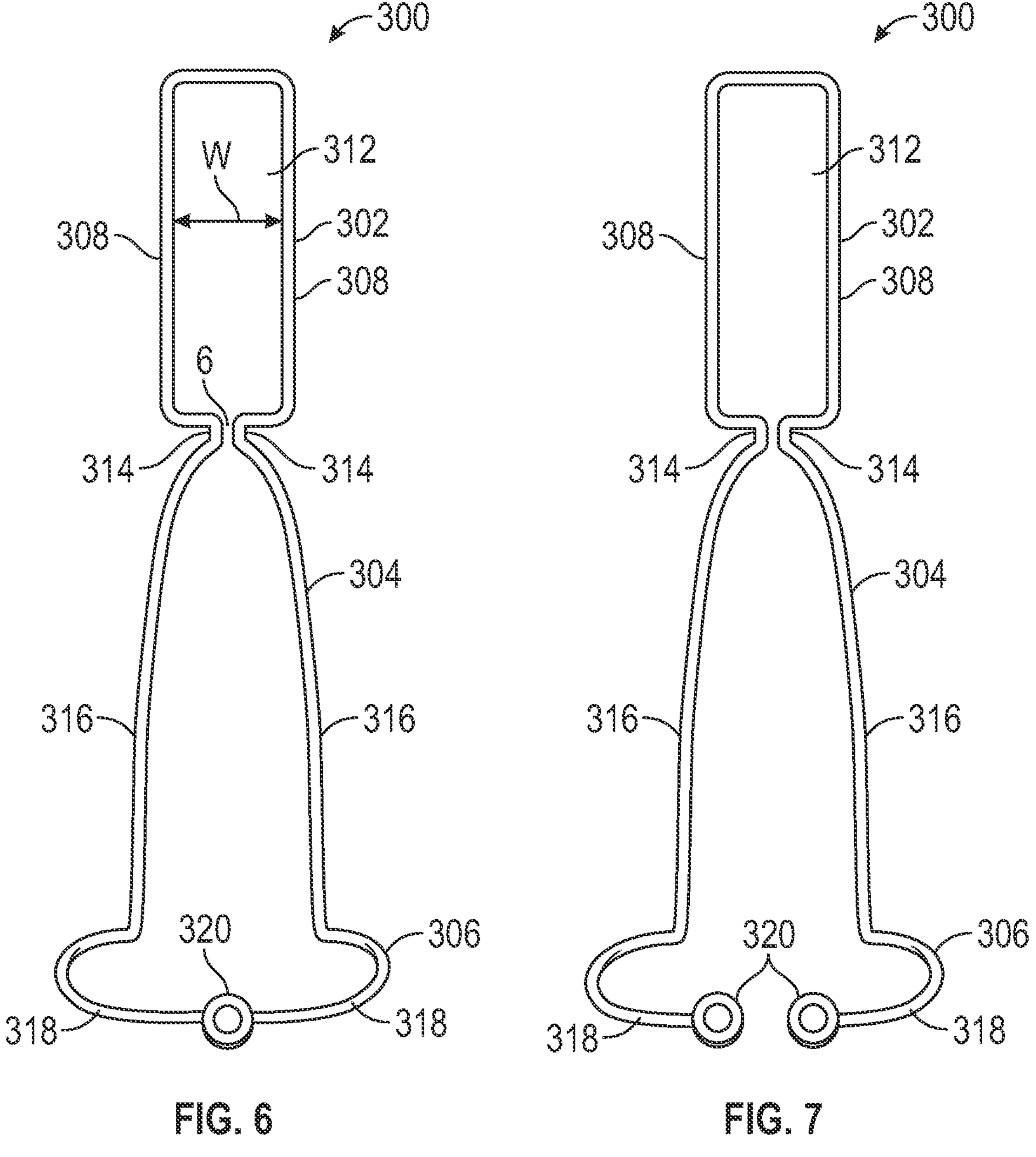
FIG. 6 is a front elevation view of a commissure attachment element, according to one example, with the lower ring segments of the commissure attachment element shown in a closed position.
FIG. 7 is a front elevation view of the commissure attachment element of FIG. 6 with the lower ring segments of the commissure attachment element shown in an open position.

FIGS. 6 and 7 show a commissure attachment member 300 (also referred to as a commissure clamp or commissure attachment elements in some embodiments) that can be used to mount a commissure of a leaflet assembly for sliding movement relative to a commissure support of a frame. The commissure attachment member 300 in the illustrated embodiment comprises an upper portion 302, an intermediate portion 304, and a lower portion 306. The upper portion 302 comprises two vertical or axial segments 308 extending from respective ends of a lateral segment 310 that interconnects the axial segments 308 at the upper end of the upper portion 302. The axial segments 308 and the lateral segment 310 define a leaflet-receiving opening 312 (also referred to as a commissure window) for receiving a pair of commissure tabs, as further described below.

At the lower end of the upper portion 302, each axial segment 308 can transition into a lateral protrusion 314, which then transitions into a respective axial segment 316 of the intermediate portion 304. The lateral protrusions 314 extend toward each other to define a gap G that desirably is smaller than the width W of the leaflet-receiving opening 312. Each axial segment 316 transitions into a respective ring segment 318 of the lower portion 306 of the commissure attachment member 300. Each ring segment 318 extends radially (perpendicular to the plane of the page of FIGS. 6-7) from the lower end of a corresponding axial segment 316. As best shown in FIG. 7, each ring segment 318 has a free end portion 320.

In a natural or non-deformed state of the commissure attachment member, which is depicted in FIG. 6, the free end portions 320 can overlap each other with one free end portion 320 positioned behind the other. As shown in FIG. 7, which shows a deformed state of the commissure attachment member, the free end portions 320 can be separated or splayed apart from each other to create a gap between them, which can allow the ring segments 318 to be placed around an actuator 150 during assembly of the prosthetic valve, as further described below.

The free end portions 320 desirably are shaped to form a connection element or feature configured to engage a corresponding feature of a frame of a prosthetic valve, the significance of which is described below. In the illustrated embodiment, each free end portion 320 is shaped as a ring configured to be placed on a pin or rivet of a pivot joint of the frame of a prosthetic valve (as shown in FIG. 10B). In other embodiments, the free end portions can have other shapes, such as in the form of a hook or a C-shape configured to be placed on a pin.

In particular embodiments, the commissure attachment member 300 can be formed of a base material bent or otherwise formed (e.g., molding, casting, machining, etc.) into the configuration illustrated in FIGS. 6-7. For example, the attachment member 300 can be formed by bending a flexible straight rod or wire, e.g., a wire formed of a metal or metal alloy, such as stainless steel, titanium, a nickel-titanium alloy (e.g., Nitinol) or any other biocompatible metal material. When formed from a bent wire, the attachment member 300 can be referred to as a "wireform" frame. Although a circular cross-section for the base material is illustrated in FIGS. 6-7, other cross-sectional shapes are also possible according to one or more embodiments. In some embodiments, all surfaces, or at least some surfaces (e.g., those surfaces that contact leaflet tabs 204) are designed as smooth surfaces so as to minimize, or at least reduce, the likelihood of abrasion due to contact with the leaflets. For example, smooth surfaces of the attachment member 300 contacting the leaflets may be substantially flat or curved without any edges or projections. Alternatively or additionally, smooth surfaces of the clamp attachment member 300 may have a relatively low surface roughness. In some embodiments, the attachment member 300 can include a coating (e.g., polymer layer) over the base material to enhance the surface smoothness or friction properties thereof.

Although the commissure attachment member 300 in the illustrated embodiment is formed from a single, continuous piece of material (e.g., a wire or rod), this is not required. In other embodiments, the commissure attachment member 300 can be formed from multiple components that are separately formed and subsequently attached to each other. For example, the upper portion 302, the intermediate portion 304, and the lower portion 306 and/or components thereof can be separately formed components that are connected to each other during manufacture of the commissure attachment member or assembly of the prosthetic valve.

Figure 8:
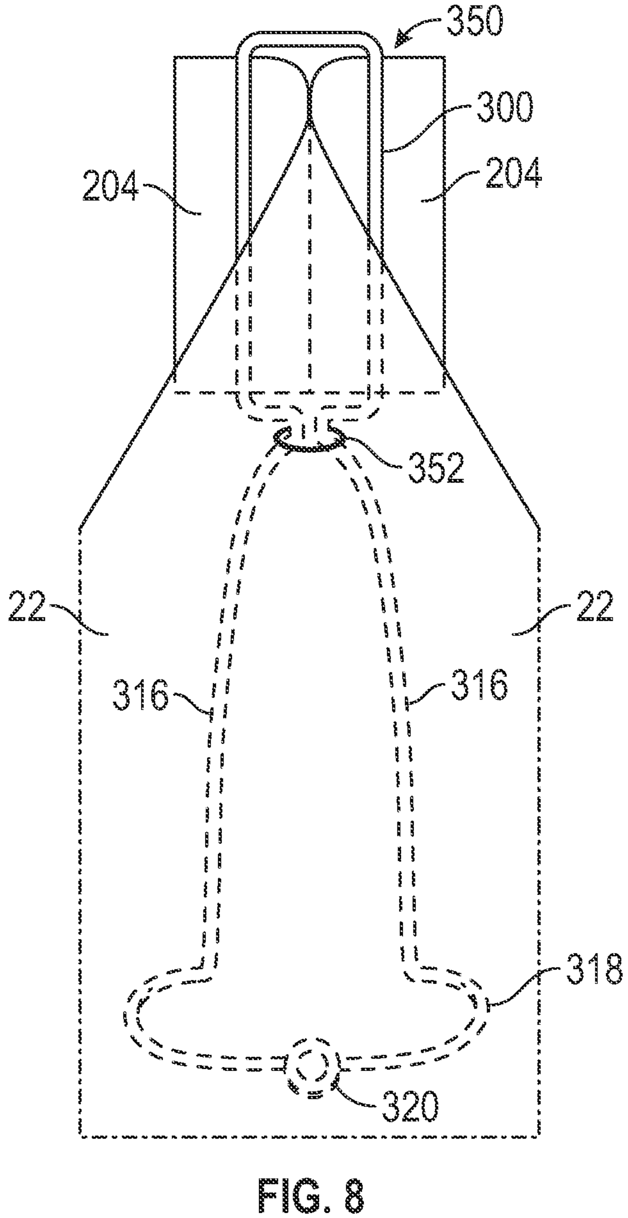
FIG. 8 is a front elevation view of a commissure formed by two leaflets and the commissure attachment element of FIG. 6.

FIG. 8 shows a commissure 350 formed by a pair of commissure tabs 204 of two leaflets 22 and a commissure attachment member 300. To form the commissure, a pair of commissure tabs 204 from two leaflets 22 are placed side-by-side and inserted into the commissure window 312 of the attachment member 300. When inserting the pair of commissure tabs, the ring segments 318 can be separated from each other (as shown in FIG. 7), and the commissure tabs can be inserted upwardly through the gap between the free end portions 320, the space between the axial segments 316, the gap G between the inward protrusions 314, and into the commissure window 312. The inward protrusions 314 can be secured to each other with a tether 352, such as a suture or wire, that can be wrapped around the two protrusions 314 to form one or more loops around the protrusions to bring them into contact or into closer proximity with each other. The tether 322 helps maintain the axial segments 308 in a parallel relationship and prevents the commissure tabs 204 from sliding out of the commissure window 312.

Figure 9A:
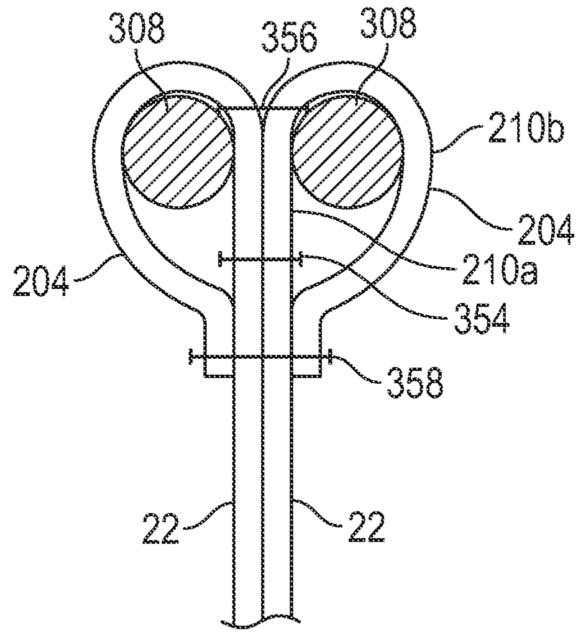
FIG. 9A is a cross-sectional view of the commissure of FIG. 8.
Figure 9B:
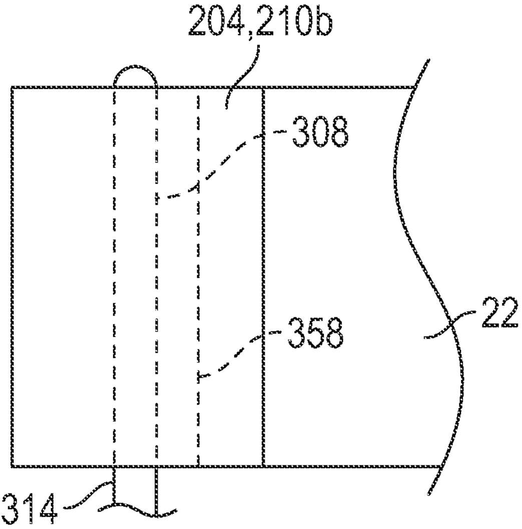
FIG. 9B is a side view of the upper portion of the commissure of FIG. 8.

One or more stitching lines can be added to secure the commissure tabs 204 to each other and the attachment member 300. For example, as shown in FIGS. 9A and 9B, optionally, one or more sutures can be used to form a first stitching line 354 that secures the commissure tabs 204 to each other radially inside of the attachment member. The first stitching line 354 can extend the height of the commissure tabs 204. Optionally, one or more sutures can be used to form a second stitching ling 356 to secure the commissure tabs 204 to each other radially outside of the attachment member. The second stitching line 356 can extend the height of the commissure tabs 204.

Each commissure tab 204 can be folded around a respective axial segment 308 to form an inner tab layer 210*a* and an outer tab layer 210*b*. Optionally, one or more sutures can be used to form a third stitching line 358 to secure the inner and outer tab layers 210*a*, 210*b* of each tab 204 to each other and to the inner and outer tab layers 210*a*, 210*b* of the other tab 204; that is, each stitch can extend through an outer tab layer 210*b* and an inner tab layer 210*a* of a first commissure tab 204, and then through the inner tab layer 210*a* and the outer tab layer 210*b* of the other commissure tab 204, in that order. The third stitching line 358 can extend the height of the commissure tabs 204. The third stitching line 358 or an additional fourth stitching line can be used to secure the pair of adjacent lower commissure portions 210 to each other.

The stitching lines 354, 356, and 358 can comprise any various suitable stitches, such as a series of in-and-out lines that extend in a direction along the height of the commissure tabs 204.

In particular embodiments, a plurality of leaflets 22 and a plurality of commissure attachment members 300 are assembled to form a leaflet assembly with a plurality of commissures 350 prior to mounting the leaflet assembly to a frame of a prosthetic heart valve. In this manner, the commissures 350 are said to be "pre-assembled" prior to mounting the leaflets to the frame. For example, in particular embodiments, a leaflet assembly can comprise three leaflets 22 that are connected to each other at adjacent commissure tabs 204, by forming three commissures 350 as described above, each having a respective commissure attachment member 300.

In certain embodiments, the pre-assembled leaflet assembly can include an inner skirt 20. For example, prior to or after forming each commissure 350, the cusp edge portion 202 of each leaflet can be sutured to the skirt 20 along a scallop line 36 (see FIG. 1). After forming the commissures 350 and optionally attaching the inner skirt to the leaflets, the leaflet assembly can be placed inside of a frame, such as frame 12 or 102. Each commissure attachment member 300 of the leaflet assembly can be mounted on a respective commissure support portion of the frame, such as a portion of an actuator. Each commissure attachment member 300 and commissure 350 can be mounted for sliding movement relative to a respective commissure support portion when the frame is radially compresses or radially expanded. The inner skirt 20 can be secured to the frame, such as with sutures 34 in the manner shown in FIG. 1.

Figure 10A:
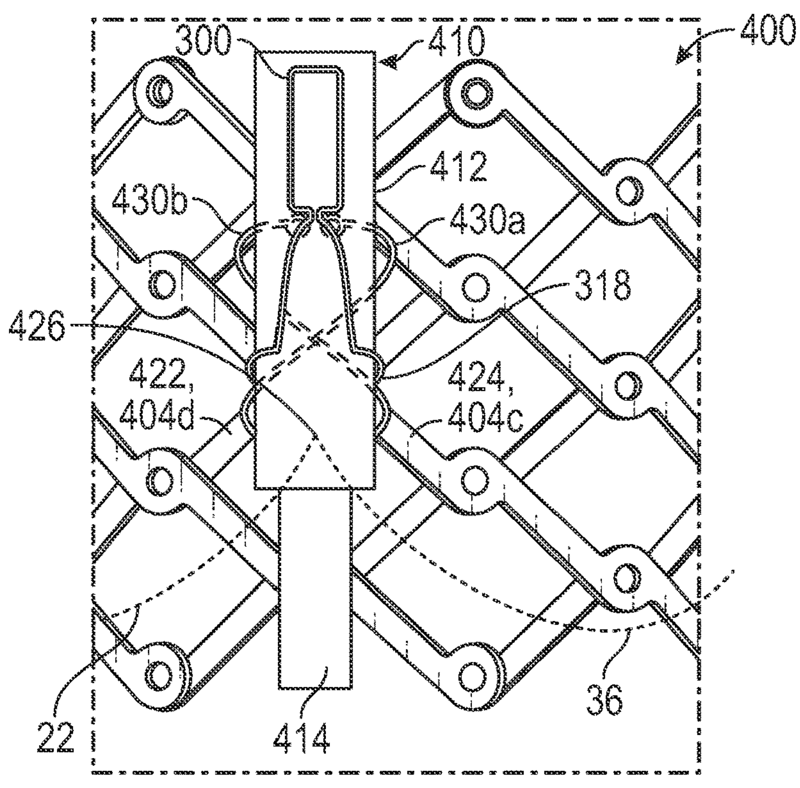
FIG. 10A is an elevation view of the inside of a prosthetic heart valve that includes the commissure of FIG. 8 mounted on an actuator of the prosthetic heart valve.
Figure 10B:
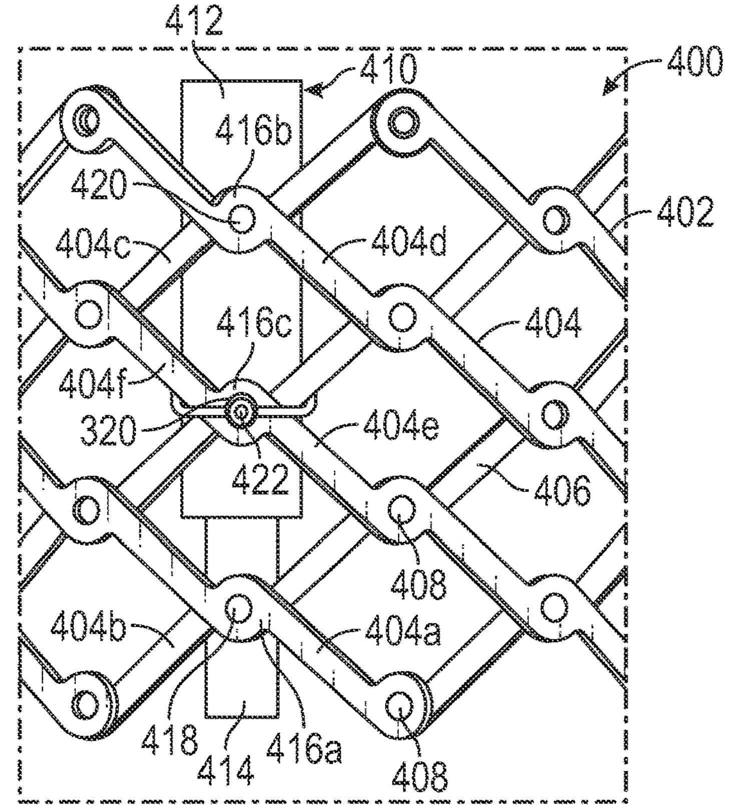
FIG. 10B is an elevation view of the outside of the prosthetic heart valve of FIG. 10A.

FIGS. 10A and 10B shows a prosthetic heart valve 400 that includes the leaflet assembly with pre-assembled commissures 350, according to one embodiment. The prosthetic heart valve 400 includes a radially expandable and compressible frame 402 comprising a plurality of struts 406 that are pivotably connected to each other with a plurality of pins or rivets 408 to form a plurality of pivot joints. The frame 402 can have the same construction as frames 12, 102 previously described. The prosthetic heart valve 400 can include a plurality of actuators 410 (one of which is shown in FIGS. 10A and 10B) pivotably coupled to selected pivot joints of the frame for radially expanding and compressing the frame and optionally for locking the frame in a radially expanded state. Each commissure 350 can be slidably mounted on a respective actuator 410. For purposes of illustration, the commissure attachment member 300 is shown but the leaflets 22 are omitted in FIGS. 10A and 10B.

Each actuator 410 can have an outer member 412 and an inner member 414 that can slide relative to the outer member 412. In particular embodiments, the actuator 410 has the same construction as actuator 150. Thus, the outer member 412 can be the same as outer member 152 and the inner member 414 can be the same as the inner member 154.

As shown in FIG. 10B, the inner member 414 can be pivotably coupled to a pivot joint 416*a* formed by two overlapping struts 404*a*, 404*b* by a fastener 418 that is connected to the inner member 414 and extends radially outward through respective apertures in the struts 404*a*, 404*b* (similar to fastener 160 of FIG. 3). The outer member 412 can be pivotably coupled to a pivot joint 416*b* formed by two overlapping struts 404*c*, 404*d* by a fastener 420 that is connected to the outer member 412 and extends radially outward through respective apertures in the struts 404*c*, 404*d* (similar to fastener 161 of FIG. 3).

Each commissure attachment member 300 of the leaflet assembly (which can include a fully formed commissure 350) can be mounted on an outer member 412 of a respective actuator 410 by placing the commissure attachment member 300 against the inner surface of the outer member 412 (the surface facing the central axis of the frame). The ring segments 318 of the commissure attachment member 300 are separated from each other and placed around the outer member 412 by inserting each ring segment 318 through an opening in the frame so as to position each free end portion 320 on the outside of the frame 402, as shown in FIG. 10B.

Both free end portions 320 can then be connected to a pivot joint 416*c* formed by two overlapping struts 404*e*, 404*f* by a fastener 422 (which can be, for example, a pin or rivet). The pivot joint 416*c* desirably is located axially between the pivot joint 416*a* and 416*b* along an axis that intersects all three pivot joints 416*a*, 416*b*, 416*c*. The free end portions 320 can be connected to the pivot joint 416*c* by placing each free end portion 320 (which can be in the shape of a ring) on the fastener 422 such that the fastener extends through the central opening of each free end portion. In this manner, the free end portions 320 (and therefore the commissure attachment member) is fixed against axial movement relative to the pivot joint 416*c*. As noted above, the free end portions 320 can have various other shapes that serve as a connection element for connecting to the fastener 422. For example, the free end portions 320 can be hook-shaped or C-shape for placement around the fastener 422.

The commissure attachment member 300 can be secured against lateral movement relative to the upper member 412 by one or more tethers 430*a*, 430*b*, which can be sutures, wires, cables, yarns, etc. Each tether 430*a* can have an upper end portion tied off or otherwise secured to an upper portion of an axial segment 316, extend helically around the upper member 412 and a lower end portion tied off or otherwise secured to a lower potion of the other axial segment 316. In this manner, the two tethers 430*a*, 430*b* can overlap or cross over each other on the outside of the outer member 412.

The scallop line 36 in FIG. 10A represents the stitching that secures the cusp edge portions 202 of the leaflets to the inner skirt 20. Although not shown in FIGS. 10A and 10B, the inner skirt 20 of the leaflet assembly can be secured to selected struts of the frame 402 with sutures 34 in the manner shown in FIG. 1. The outflow edge portion of the skirt (the upper edge portion in the illustrated embodiment) can be secured to strut segment 424 of strut 404*f* and strut segment 426 of strut 404*e* at pivot point 416*c*. The peak 426 of the scallop line 36 (where the upper-most ends of adjacent cusp edge portions are secured to the skirt) desirably extends at least to the height of the pivot joint 416*c*, and more desirably at least to the height of the fastener 422 of the pivot joint 416*c*. In this manner, the peak 426 of the scallop line is fixed relative to the pivot joint 416*b*, the fastener 422, and the commissure attachment member 300.

The frame 402 can be radially expanded and compressed upon actuation of the actuators 410, as described above in connection with the prosthetic valve 100. Thus, when the frame is radially compressed, the inner member 414 moves distally (downward in FIGS. 10A and 10B) relative to the outer member 412 and/or the outer member 412 moves proximally (upward in FIGS. 10A and 10B), which causes the pivot joints 416*a*, 416*b* to move away from each other. Conversely, when the frame is radially expanded, the inner member 414 moves proximally (upward in FIGS. 10A and 10B) relative to the outer member 412 and/or the outer member 412 moves distally (downward in FIGS. 10A and 10B), which causes the pivot joints 416*a*, 416*b* to closer toward each other.

As the outer member 412 moves relative to the inner member 414 during radially compression and expansion of the frame, the commissure attachment member 300 (which is retained at a fixed location relative to the fastener 422 and the pivot joint 416*c*) and the outer member 412 can slide axially relative to each other. This allows the commissure 350 and the outer member 412 to slide axially relative to each other during radial expansion and compression of the frame. Advantageously, this avoids deformation of the commissure portions of the leaflets (commissure tabs 204 and/or the lower commissure portions 210) in an axial direction upon radial expansion and compression of the frame. Stated differently, the commissure 350 (and each commissure tab 204 and lower commissure portion 210) can maintain a fixed height upon radial expansion and compression of the frame, which avoids stretching of the commissure tabs and the lower commissure portions during radial compression and/or the formation of slack in the commissure tabs during radial expansion. The commissure 350 can also maintain a fixed height relative to the peak 426 of the scallop line 36, which avoids deformation of the lower commissure portions 210 relative to the cusp edge portions 202 during radial compression and radial expansion of the frame.

In alternative embodiments, the commissure attachment element 300 can be connected to the frame at the same location where the inner member 414 of the actuator is connected to the frame; for example, both can be connected to the same fastener that forms one of the pivot joints of the frame. In one implementation, for example, both the inner member 414 and the free end portions 320 can be connected to the fastener 422 at pivot joint 416*c*, which would still permit relative axial movement between the commissure attachment element 300 and the outer member 412 of the actuator. In another implementation, both the inner member 414 and the free end portions 320 can be connected to the fastener 418 at pivot joint 416*a*, which would still permit relative axial movement between the commissure attachment element 300 and the outer member 412 of the actuator.

In alternative embodiments, the cusp edge portion 202 of each leaflet can extend to and intersect the commissure tabs 204. Thus, when the leaflet assembly is formed, the adjacent leaflets 22 are not connected along lower commissure portions 210 and instead the peak 426 of the scallop line 36 can extend to the lower edges of the commissure tabs 204. In such embodiments, the commissure attachment element 300 can be modified such that the axial segments 316 are shortened or eliminated such that the lower segments 318 are closer to the lateral protrusions 314 or extend directly from the lateral protrusions 314. When the leaflet assembly are mounted on the frame with the free end portions 320 of each commissure attachment member connected to fastener 422, the lower edges of the commissure tabs 204 can be at or about the same height of the fastener 422.

In alternative embodiments, a prosthetic heart valve can comprise a frame and a leaflet assembly having multiple commissures 350, wherein the commissure attachment members 300 are slidably mounted on commissure support portions that are not components of an actuator. For example, a frame of a prosthetic valve (e.g., frame 12, 102, 402) can have one or more commissure support posts, each of which can be coupled to a pivot joint of the frame (similar to the actuators) and each commissure attachment member 300 can be slidably mounted on a respective post. In one specific implementation, a commissure support post can replace the actuator 410 in FIGS. 10A and 10B and can be attached to the frame at pivot joint 416*b*, and a commissure support member 300 can be slidably mounted on the commissure support port and connected to the pivot joint 416*c*. The prosthetic valve can have actuators (e.g., actuators 80, 150, 410) coupled to other locations of the frame for radially compressing and expanding the prosthetic valve.

In alternative embodiments, a prosthetic valve can have a frame comprising a plurality of integrally formed struts, such as a laser cut frame, such as disclosed U.S. Pat. No. 9,393,110 and U.S. Publication No. 2018/0028310. The prosthetic valve can have a plurality of commissure support posts and/or actuators (e.g., actuators 80, 150, 410) coupled to the struts of the frame for radially expanding and compressing the prosthetic valve and a leaflet assembly with commissure attachment members 300 slidably mounted on the commissure support posts or the actuators as described above. In alternative embodiments, the commissure support posts can be integral components of the frame.

Figure 11:
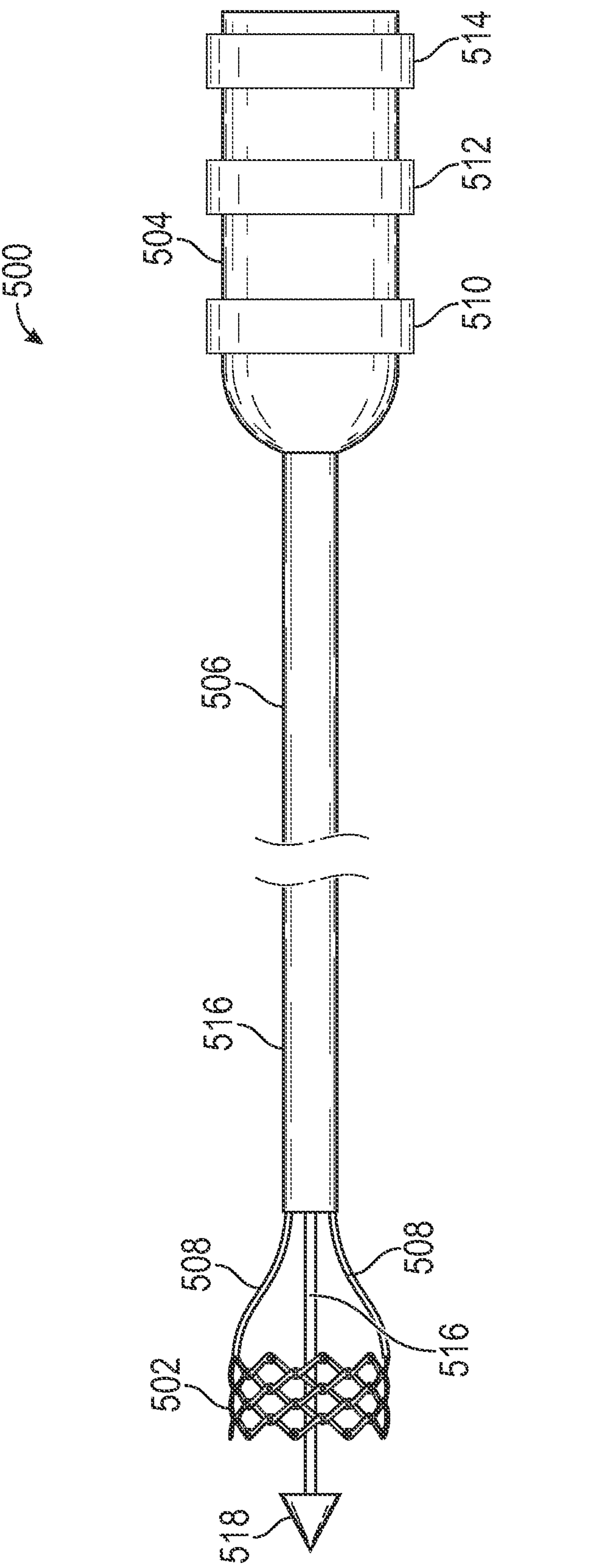
FIG. 11 is a side elevation view of a delivery apparatus for a prosthetic heart valve, according to one example.

FIG. 11 illustrates a delivery apparatus 500, according to one example, adapted to deliver a prosthetic heart valve 502 (e.g., valve 10, 100, or 400). The prosthetic valve 502 can be releasably coupled to the delivery apparatus 500. It should be understood that the delivery apparatus 500 and other delivery apparatuses disclosed herein can be used to implant prosthetic devices other than prosthetic valves, such as stents or grafts.

The delivery apparatus 500 in the illustrated embodiment generally includes a handle 504, a first elongated shaft 506 (which comprises an outer shaft in the illustrated example) extending distally from the handle 504, at least one actuator assembly 508 extending distally from the handle through the outer shaft 506, and a second elongated shaft 516 (which comprises an inner shaft in the illustrated example) extending distally from the handle through the outer shaft 506. The at least one actuator assembly 508 can be configured to radially expand and/or radially collapse the prosthetic valve 502 when actuated. A nosecone 518 can be mounted to the distal end of the second shaft 516. The second shaft 516 and the nosecone 518 can define a guidewire lumen sized for receiving a guidewire so that the delivery apparatus can be advanced over a guidewire previously inserted into a patient's body.

Though the illustrated embodiment shows two actuator assemblies 508 for purposes of illustration, it should be understood that one actuator 508 can be provided for each actuator on the prosthetic valve. For example, three actuator assemblies 508 can be provided for a prosthetic valve having three actuators. In other embodiments, a greater or fewer number of actuator assemblies can be present.

In some embodiments, a distal end portion 516 of the shaft 506 can be sized to house the prosthetic valve in its radially compressed, delivery state during delivery of the prosthetic valve through the patient's vasculature. In this manner, the distal end portion 516 functions as a delivery sheath or capsule for the prosthetic valve during delivery, The actuator assemblies 508 can be releasably coupled to the prosthetic valve 502. For example, in the illustrated embodiment, each actuator assembly 508 can be coupled to a respective actuator of the prosthetic valve 502. Each actuator assembly 508 can comprise a support tube, an actuator member, and optionally a locking tool. When actuated, the actuator assembly can transmit pushing and/or pulling forces to portions of the prosthetic valve to radially expand and collapse the prosthetic valve as previously described. The actuator assemblies 508 can be at least partially disposed radially within, and extend axially through, one or more lumens of the outer shaft 506. For example, the actuator assemblies 508 can extend through a central lumen of the shaft 506 or through separate respective lumens formed in the shaft 506.

The handle 504 of the delivery apparatus 500 can include one or more control mechanisms (e.g., knobs or other actuating mechanisms) for controlling different components of the delivery apparatus 100 in order to expand and/or deploy the prosthetic valve 502. For example, in the illustrated embodiment the handle 504 comprises first, second, and third knobs 510, 512, and 514.

The first knob 510 can be a rotatable knob configured to produce axial movement of the outer shaft 506 relative to the prosthetic valve 502 in the distal and/or proximal directions in order to deploy the prosthetic valve from the delivery sheath 516 once the prosthetic valve has been advanced to a location at or adjacent the desired implantation location with the patient's body. For example, rotation of the first knob 510 in a first direction (e.g., clockwise) can retract the sheath 516 proximally relative to the prosthetic valve 502 and rotation of the first knob 510 in a second direction (e.g., counter-clockwise) can advance the sheath 516 distally. In other embodiments, the first knob 510 can be actuated by sliding or moving the knob 510 axially, such as pulling and/or pushing the knob. In other embodiments, actuation of the first knob 510 (rotation or sliding movement of the knob 510) can produce axial movement of the actuator assemblies 508 (and therefore the prosthetic valve 502) relative to the delivery sheath 516 to advance the prosthetic valve distally from the sheath 516.

The second knob 512 can be a rotatable knob configured to produce radial expansion and/or contraction of the prosthetic valve 502. For example, rotation of the second knob 512 can move the actuator member and the support tube axially relative to one another. Rotation of the second knob 512 in a first direction (e.g., clockwise) can radially expand the prosthetic valve 502 and rotation of the second knob 512 in a second direction (e.g., counter-clockwise) can radially collapse the prosthetic valve 502. In other embodiments, the second knob 512 can be actuated by sliding or moving the knob 512 axially, such as pulling and/or pushing the knob.

The third knob 514 can be a rotatable knob configured to retain the prosthetic heart valve 102 in its expanded configuration. For example, the third knob 514 can be operatively connected to a proximal end portion of the locking tool of each actuator assembly 508. Rotation of the third knob in a first direction (e.g., clockwise) can rotate each locking tool to advance the locking nuts to their distal positions to resist radial compression of the frame of the prosthetic valve, as described above. Rotation of the knob 514 in the opposite direction (e.g., counterclockwise) can rotate each locking tool in the opposite direction to decouple each locking tool from the prosthetic valve 502. In other embodiments, the third knob 514 can be actuated by sliding or moving the third knob 514 axially, such as pulling and/or pushing the knob.

Although not shown, the handle 504 can include a fourth rotatable knob operative connected to a proximal end portion of each actuator member. The fourth knob can be configured to rotate each actuator member, upon rotation of the knob, to unscrew each actuator member from the proximal portion of a respective actuator. As described above, once the locking tools and the actuator members are uncoupled from the prosthetic valve 502, they can be removed from the patient.

Delivery Techniques

For implanting a prosthetic valve within the native aortic valve via a transfemoral delivery approach, the prosthetic valve is mounted in a radially compressed state along the distal end portion of a delivery apparatus. The prosthetic valve and the distal end portion of the delivery apparatus are inserted into a femoral artery and are advanced into and through the descending aorta, around the aortic arch, and through the ascending aorta. The prosthetic valve is positioned within the native aortic valve and radially expanded (e.g., by inflating a balloon, actuating one or more actuators of the delivery apparatus, or deploying the prosthetic valve from a sheath to allow the prosthetic valve to self-expand). Alternatively, a prosthetic valve can be implanted within the native aortic valve in a transapical procedure, whereby the prosthetic valve (on the distal end portion of the delivery apparatus) is introduced into the left ventricle through a surgical opening in the chest and the apex of the heart and the prosthetic valve is positioned within the native aortic valve. Alternatively, in a transaortic procedure, a prosthetic valve (on the distal end portion of the delivery apparatus) are introduced into the aorta through a surgical incision in the ascending aorta, such as through a partial J-sternotomy or right parasternal mini-thoracotomy, and then advanced through the ascending aorta toward the native aortic valve.

For implanting a prosthetic valve within the native mitral valve via a transseptal delivery approach, the prosthetic valve is mounted in a radially compressed state along the distal end portion of a delivery apparatus. The prosthetic valve and the distal end portion of the delivery apparatus are inserted into a femoral vein and are advanced into and through the inferior vena cava, into the right atrium, across the atrial septum (through a puncture made in the atrial septum), into the left atrium, and toward the native mitral valve. Alternatively, a prosthetic valve can be implanted within the native mitral valve in a transapical procedure, whereby the prosthetic valve (on the distal end portion of the delivery apparatus) is introduced into the left ventricle through a surgical opening in the chest and the apex of the heart and the prosthetic valve is positioned within the native mitral valve.

For implanting a prosthetic valve within the native tricuspid valve, the prosthetic valve is mounted in a radially compressed state along the distal end portion of a delivery apparatus. The prosthetic valve and the distal end portion of the delivery apparatus are inserted into a femoral vein and are advanced into and through the inferior vena cava, and into the right atrium, and the prosthetic valve is positioned within the native tricuspid valve. A similar approach can be used for implanting the prosthetic valve within the native pulmonary valve or the pulmonary artery, except that the prosthetic valve is advanced through the native tricuspid valve into the right ventricle and toward the pulmonary valve/pulmonary artery.

Another delivery approach is a transatrial approach whereby a prosthetic valve (on the distal end portion of the delivery apparatus) is inserted through an incision in the chest and an incision made through an atrial wall (of the right or left atrium) for accessing any of the native heart valves. Atrial delivery can also be made intravascularly, such as from a pulmonary vein. Still another delivery approach is a transventricular approach whereby a prosthetic valve (on the distal end portion of the delivery apparatus) is inserted through an incision in the chest and an incision made through the wall of the right ventricle (typically at or near the base of the heart) for implanting the prosthetic valve within the native tricuspid valve, the native pulmonary valve, or the pulmonary artery.

In all delivery approaches, the delivery apparatus can be advanced over a guidewire and/or an introducer sheath previously inserted into a patient's vasculature. Moreover, the disclosed delivery approaches are not intended to be limited. Any of the prosthetic valves disclosed herein can be implanted using any of various delivery procedures and delivery devices known in the art.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A prosthetic heart valve comprising:

an annular frame comprising a plurality of interconnected struts, wherein the frame is radially compressible and expandable between a radially compressed state and a radially expanded state, wherein the frame comprises a plurality of commissure support portions;

a plurality of leaflets situated within the frame, each leaflet comprising a body and two opposing commissure tabs arranged on opposite sides of the body; and a plurality of commissure attachment elements, wherein each commissure tab of a leaflet is paired with an adjacent commissure tab of an adjacent leaflet and the pair of commissure tabs are connected to one of the commissure attachment elements to form a plurality of commissures;

wherein each commissure attachment element is slidably mounted on one of the commissure support portions such that the commissures can slide axially relative to the commissure support portions when the frame is radially expanded and compressed between the radially compressed state and the radially expanded state.

Example 2. The prosthetic heart valve of any example herein, particularly example 1, wherein the frame comprises a plurality of actuators, each comprising first and second members that are axially moveable relative to each other to produce radial expansion and compression of the frame, wherein commissure support portions are the first members of the actuators.

Example 3. The prosthetic heart valve of any example herein, particularly example 2, wherein the struts comprise a plurality of first struts overlapping and pivotably connected to a plurality of second struts at a plurality of pivot joints, and for each actuator, the first member is connected to a first pivot joint and the second member is connected to a second pivot joint axially spaced from the first pivot joint and each commissure attachment element is connected to a third pivot joint positioned axially between the first pivot joint and the second pivot joint such that the commissure attachment element is retained against axial movement relative to the third pivot joint upon radial expansion and compression of the frame.

Example 4. The prosthetic heart valve of any example herein, particularly example 3, wherein each third pivot joint comprises a pin coupling a pair of first and second overlapping struts and each commissure attachment element is connected to the pin at a corresponding third pivot joint.

Example 5. The prosthetic heart valve of any example herein, particularly example 4, wherein each commissure attachment element comprises a commissure window frame portion that retains a pair of commissure tabs of a corresponding commissure and two free end portions that are disposed on the pin at a corresponding third pivot joint.

Example 6. The prosthetic heart valve of any example herein, particularly example 5, wherein for each commissure attachment element, the commissure window frame portion is disposed inside of a corresponding first member and the free end portions are disposed outside of the frame.

Example 7. The prosthetic heart valve of any example herein, particularly any of examples 5-6, wherein the free end portions of each commissure attachment element are rings and the pin at each third pivot joint extends through the rings of a corresponding commissure attachment element.

Example 8. The prosthetic heart valve of any example herein, particularly any of examples 3-7, further comprising an inner skirt connected to the frame, and each leaflet has a cusp edge portion stitched to the skirt along a scallop line having a plurality of peaks located at the third pivot joints.

Example 9. The prosthetic heart valve of any example herein, particularly example 8, wherein the skirt has an outflow edge portion that is stitched to struts forming the third pivot joints.

Example 10. The prosthetic heart valve of any example herein, particularly any one of examples 1-9, wherein each commissure attachment element comprises a wireform frame.

Example 11. The prosthetic heart valve of any example herein, particularly any one of examples 2-10, wherein the first members of the actuators are outer sleeves and the second members are inner members that are movable axially within the outer sleeves.

Example 12. A prosthetic heart valve comprising:

an annular frame comprising a plurality of first struts overlapping and pivotably connected to a plurality of second struts at a plurality of pivot joints, wherein the frame is radially compressible and expandable between a radially compressed state and a radially expanded state;

wherein the frame comprises a plurality of actuators, each comprising first and second members that are axially moveable relative to each other to produce radial expansion and compression of the frame;

a plurality of leaflets situated within the frame, each leaflet comprising a body and two opposing commissure tabs arranged on opposite sides of the body; and a plurality of commissure attachment elements, wherein each commissure tab of a leaflet is paired with an adjacent commissure tab of an adjacent leaflet and the pair of commissure tabs are connected to one of the commissure attachment elements to form a plurality of commissures; wherein each commissure attachment element is slidably mounted on the first member of one of the actuators such that the commissures can slide axially relative to the first members when the frame is radially expanded and compressed between the radially compressed state and the radially expanded state.

Example 13. The prosthetic heart valve of any example herein, particularly example 12, wherein each pivot joint comprises a pin coupling one of the first struts with one of the second struts and each commissure attachment element is retained by one of the pins.

Example 14. The prosthetic heart valve of any example herein, particularly example 13, wherein each commissure attachment element comprises a commissure window frame portion that retains a pair of commissure tabs of a corresponding commissure and two free end portions that are disposed on the pin at a corresponding pivot joint.

Example 15. The prosthetic heart valve of any example herein, particularly example 14, wherein for each commissure attachment element, the commissure window frame portion is disposed inside of a corresponding first member and the free end portions are disposed outside of the frame.

Example 16. The prosthetic heart valve of any example herein, particularly any one of examples 13-15, further comprising an inner skirt connected to the frame, and each leaflet has a cusp edge portion stitched to the skirt along a scallop line having a plurality of peaks located at the pivot joints retaining the commissure attachment elements.

Example 17. The prosthetic heart valve of any example herein, particularly example 16, wherein the skirt has an outflow edge portion that is stitched to struts forming the pivot joints retaining the commissure attachment elements.

Example 18. The prosthetic heart valve of any example herein, particularly any one of examples 13-17, wherein the pins comprise a plurality of first pins, second pins and third pins, the first member of each actuator is connected to one of the first pins, the second member of each actuator is connected to one of the second pins, and each commissure attachment element is connected to one of the third pins, which is located axially between a first pin and a second pin.

Example 19. The prosthetic heart valve of any example herein, particularly any one of examples 12-18, wherein the first members of the actuators are outer sleeves and the second members are inner members that are movable axially within the outer sleeves.

Example 20. A prosthetic heart valve comprising:

an annular frame comprising a plurality struts, wherein the frame is radially compressible and expandable between a radially compressed state and a radially expanded state;

wherein the frame comprises a plurality of actuators, each comprising first and second members that are axially moveable relative to each other to produce radial expansion and compression of the frame;

a plurality of leaflets situated within the frame, each leaflet comprising a body having a cusp edge portion and two opposing commissure tabs arranged on opposite sides of the body; and a plurality of commissure attachment elements, wherein each commissure tab of a leaflet is paired with an adjacent commissure tab of an adjacent leaflet and the pair of commissure tabs are connected to one of the commissure attachment elements to form a plurality of commissures; wherein each commissure attachment element is slidably mounted on the first member of one of the actuators such that the commissures can slide axially relative to the first members when the frame is radially expanded and compressed between the radially compressed state and the radially expanded state.

Example 21. The prosthetic heart valve of any example herein, particularly example 20, wherein the first members are connected to respective first joints between struts, the second members are connected to respective second joints between struts, and the commissure attachment elements are connected to respective third joints, each of which is located axially between one of the first joints and one of the second joints, wherein the commissure attachment elements are retained against axial movement relative to the third joints upon radial expansion and compression of the frame.

Example 22. The prosthetic heart valve of any example herein, particularly example 21, wherein the struts comprise a plurality of first struts overlapping and pivotably connected to a plurality of second struts at a plurality of pivot joints, wherein the first joints are first pivot joints, the second joints are second pivot joints and the third joints are third pivot joints.

Example 23. The prosthetic heart valve of any example herein, particularly example 22, wherein each commissure attachment element comprises a commissure window frame portion that retains a pair of commissure tabs of a corresponding commissure and two free end portions that are connected to a corresponding third pivot joint.

Example 24. The prosthetic heart valve of any example herein, particularly example 23, wherein for each commissure attachment element, the commissure window frame portion is disposed inside of a corresponding first member and the free end portions are disposed outside of the frame.

Example 25. The prosthetic heart valve of any example herein, particularly any one of examples 23-24, wherein the free end portions of each commissure attachment element are rings and each third pivot joint has a pin that extends through the rings of a corresponding commissure attachment element.

Example 26. The prosthetic heart valve of any example herein, particularly any one of examples 21-25, further comprising an inner skirt connected to the frame, and each leaflet has a cusp edge portion stitched to the skirt along a scallop line having a plurality of peaks located at the third joints.

Example 27. The prosthetic heart valve of any example herein, particularly example 26, wherein the skirt has an outflow edge portion that is stitched to struts forming the third joints.

Example 28. The prosthetic heart valve of any example herein, particularly any one of examples 20-27, wherein each commissure attachment element comprises a wireform frame.

Example 29. A prosthetic heart valve comprising:

an annular frame comprising a plurality of first struts overlapping and pivotably connected to a plurality of second struts at a plurality of pivot joints, wherein the frame is radially compressible and expandable between a radially compressed state and a radially expanded state;

a plurality of leaflets situated within the frame, each leaflet comprising a body and two opposing commissure tabs arranged on opposite sides of the body; and a plurality of commissure attachment elements, wherein each commissure tab of a leaflet is paired with an adjacent commissure tab of an adjacent leaflet and the pair of commissure tabs are connected to one of the commissure attachment elements to form a plurality of commissures; wherein each commissure attachment element is connected to one of the pivot joints such that the commissure attachment element is retained axially by the pivot joint when the frame is radially expanded and compressed between the radially compressed state and the radially expanded state.

Example 30. The prosthetic valve of any example herein, particularly example 29, wherein the frame comprises a plurality of actuators, each comprising first and second members that are axially moveable relative to each other to produce radial expansion and compression of the frame.

Example 31. The prosthetic heart valve of any example herein, particularly example 30, wherein each commissure attachment element is slidably mounted on the first member of one of the actuators such that the commissures can slide axially relative to the first members when the frame is radially expanded and compressed between the radially compressed state and the radially expanded state.

Example 32. The prosthetic heart valve of any example herein, particularly example 31, wherein each pivot joint comprises a pin.

Example 33. The prosthetic heart valve of any example herein, particularly example 32, wherein each commissure attachment element comprises a commissure window frame portion that retains a pair of commissure tabs of a corresponding commissure and two free end portions that are disposed on the pin at a corresponding pivot joint.

Example 34. The prosthetic heart valve of any example herein, particularly example 33, wherein for each commissure attachment element, the commissure window frame portion is disposed inside of a corresponding first member and the free end portions are disposed outside of the frame.

Example 35. The prosthetic heart valve of any example herein, particularly any one of examples 32-34, wherein the first and second members of each actuator are connected to respective pins.

Example 36. The prosthetic heart valve of any example herein, particularly any one of examples 29-35, further comprising an inner skirt connected to the frame, and each leaflet has a cusp edge portion stitched to the skirt along a scallop line having a plurality of peaks located at the pivot joints to which the commissure attachment elements are retained.

Example 37. The prosthetic heart valve of any example herein, particularly example 36, wherein the skirt has an outflow edge portion that is stitched to struts forming the pivot joints to which the commissure attachment elements are retained.

Example 38. The prosthetic heart valve of any example herein, particularly any one of examples 29-37, wherein each commissure attachment element comprises a wireform frame.

Example 39. A method of assembling a prosthetic heart valve comprising a frame and a plurality of leaflets, wherein the frame is radially compressible and expandable between a radially compressed state and a radially expanded state, the method comprising:

forming a plurality of commissures with the plurality of leaflets, each leaflet including two opposing commissure tabs arranged on opposite sides of a body of the leaflet, wherein each commissure is formed by pairing each commissure tab of each leaflet with an adjacent commissure tab of an adjacent leaflet and coupling each pair of commissure tabs to a commissure attachment member; and mounting each commissure attachment member on a commissure support portion of the frame such that the commissures and the commissure support portions can slide axially relative to each other when the frame moves from the radially compressed state and the radially expanded state, and vice versa.

Example 40. The method of any example herein, particularly example 39, wherein the frame comprises a plurality of actuators, each comprising first and second members that are axially moveable relative to each other to produce radial expansion and compression of the frame, wherein commissure support portions are the first members of the actuators.

Example 41. The method of example 40, wherein:

the struts comprise a plurality of first struts overlapping and pivotably connected to a plurality of second struts at a plurality of pivot joints, and for each actuator, the first member is connected to a first pivot joint and the second member is connected to a second pivot joint axially spaced from the first pivot joint; and mounting each commissure attachment member comprises mounting each commissure attachment member on a first member of an actuator and connecting the commissure attachment member to a third pivot joint positioned axially between a first pivot joint and a second pivot joint such that the commissure attachment element is retained against axial movement relative to the third pivot joint upon radial expansion and compression of the frame.

Example 42. The method of any example herein, particularly example 41, wherein each third pivot joint comprises a pin coupling a pair of first and second overlapping struts of the frame and connecting each commissure attachment member to a third pivot joint comprises connecting each commissure attachment member to the pin at a corresponding third pivot joint.

Example 43. The method of any example herein, particularly example 42, wherein each commissure attachment member comprises a commissure window frame portion that retains a pair of commissure tabs of a corresponding commissure and two free end portions that are disposed on the pin at a corresponding third pivot joint.

Example 44. The method of any example herein, particularly example 43, wherein mounting each commissure attachment member comprises mounting each commissure attachment member on a first member of an actuator such that the commissure window frame portion is disposed inside of the first member and the free end portions are disposed outside of the frame.

Example 45. The method of any example herein, particularly any one of examples 43-44, wherein the free end portions of each commissure attachment element are rings and the pin at each third pivot joint extends through the rings of a corresponding commissure attachment element.

Example 46. The method of any example herein, particularly any one of examples 42-45, further comprising suturing an inner skirt to a cusp edge portion of each leaflet to form a scalloped stitching line having a plurality of peaks and coupling the inner skirt to the frame such that the peaks of the scallop line are located at the third pivot joints.

Example 47. The method of any example herein, particularly example 46, wherein coupling the inner skirt to the frame comprises connecting an outflow edge portion of the inner skirt with sutures to struts of the frame forming the third pivot joints.

Example 48. The method of any example herein, particularly any one of examples 39-47, wherein each commissure attachment element comprises a wireform frame.

Example 49. The method of any example herein, particularly any one of examples 40-48, wherein the first members of the actuators are outer sleeves and the second members are inner members that are movable axially within the outer sleeves.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A prosthetic heart valve comprising:

an annular frame comprising a plurality of interconnected struts, wherein the frame is radially compressible and expandable between a radially compressed state and a radially expanded state, wherein the frame comprises a plurality of commissure support portions;

a plurality of leaflets situated within the frame, each leaflet comprising a body and two opposing commissure tabs arranged on opposite sides of the body; and a plurality of commissure attachment elements, wherein each commissure tab of a leaflet is paired with an adjacent commissure tab of an adjacent leaflet and the pair of commissure tabs are connected to one of the commissure attachment elements to form a plurality of commissures;

wherein each commissure attachment element is slidably mounted on one of the commissure support portions such that the commissures can slide axially relative to the commissure support portions when the frame is radially expanded and compressed between the radially compressed state and the radially expanded state;

wherein the frame comprises a plurality of actuators, each comprising first and second members that are axially moveable relative to each other to produce radial expansion and compression of the frame, wherein commissure support portions are the first members of the actuators;

wherein the struts comprise a plurality of first struts overlapping and pivotably connected to a plurality of second struts at a plurality of pivot joints, and for each actuator, the first member is connected to a first pivot joint and the second member is connected to a second pivot joint axially spaced from the first pivot joint and each commissure attachment element is connected to a third pivot joint positioned axially between the first pivot joint and the second pivot joint such that the commissure attachment element is retained against axial movement relative to the third pivot joint upon radial expansion and compression of the frame.

2. The prosthetic heart valve of claim 1, wherein each third pivot joint comprises a pin coupling a pair of first and second overlapping struts and each commissure attachment element is connected to the pin at a corresponding third pivot joint.

3. The prosthetic heart valve of claim 2, wherein each commissure attachment element comprises a commissure window frame portion that retains a pair of commissure tabs of a corresponding commissure and two free end portions that are disposed on the pin at a corresponding third pivot joint.

4. The prosthetic heart valve of claim 3, wherein for each commissure attachment element, the commissure window frame portion is disposed inside of a corresponding first member and the free end portions are disposed outside of the frame.

5. The prosthetic heart valve of claim 3, wherein the free end portions of each commissure attachment element are rings and the pin at each third pivot joint extends through the rings of a corresponding commissure attachment element.

6. The prosthetic heart valve of claim 1, further comprising an inner skirt connected to the frame, and each leaflet has a cusp edge portion stitched to the skirt along a scallop line having a plurality of peaks located at the third pivot joints.

7. The prosthetic heart valve of claim 6, wherein the skirt has an outflow edge portion that is stitched to struts forming the third pivot joints.

8. The prosthetic heart valve of claim 1, wherein each commissure attachment element comprises a wireform frame.

9. The prosthetic heart valve of claim 1, wherein the first members of the actuators are outer sleeves and the second members are inner members that are movable axially within the outer sleeves.

10. A prosthetic heart valve comprising:

an annular frame comprising a plurality of first struts overlapping and pivotably connected to a plurality of second struts at a plurality of pivot joints, wherein the frame is radially compressible and expandable between a radially compressed state and a radially expanded state;

wherein the frame comprises a plurality of actuators, each comprising first and second members that are axially moveable relative to each other to produce radial expansion and compression of the frame;

a plurality of leaflets situated within the frame, each leaflet comprising a body and two opposing commissure tabs arranged on opposite sides of the body; and a plurality of commissure attachment elements, wherein each commissure tab of a leaflet is paired with an adjacent commissure tab of an adjacent leaflet and the pair of commissure tabs are connected to one of the commissure attachment elements to form a plurality of commissures;

wherein each commissure attachment element is slidably mounted on the first member of one of the actuators such that the commissures can slide axially relative to the first members when the frame is radially expanded and compressed between the radially compressed state and the radially expanded state;

wherein each pivot joint comprises a pin coupling one of the first struts with one of the second struts and each commissure attachment element is retained by one of the pins;

wherein each commissure attachment element comprises a commissure window frame portion that retains a pair of commissure tabs of a corresponding commissure and two free end portions that are disposed on the pin at a corresponding pivot joint.

11. The prosthetic heart valve of claim 10, wherein for each commissure attachment element, the commissure window frame portion is disposed inside of a corresponding first member and the free end portions are disposed outside of the frame.

12. The prosthetic heart valve of claim 10, further comprising an inner skirt connected to the frame, and each leaflet has a cusp edge portion stitched to the skirt along a scallop line having a plurality of peaks located at the pivot joints retaining the commissure attachment elements.

13. The prosthetic heart valve of claim 12, wherein the skirt has an outflow edge portion that is stitched to struts forming the pivot joints retaining the commissure attachment elements.

14. The prosthetic heart valve of claim 10, wherein the pins comprise a plurality of first pins, second pins and third pins, the first member of each actuator is connected to one of the first pins, the second member of each actuator is connected to one of the second pins, and each commissure attachment element is connected to one of the third pins, which is located axially between a first pin and a second pin.

15. The prosthetic heart valve of claim 10, wherein the first members of the actuators are outer sleeves and the second members are inner members that are movable axially within the outer sleeves.

16. A prosthetic heart valve comprising:

an annular frame comprising a plurality of first struts overlapping and pivotably connected to a plurality of second struts at a plurality of pivot joints, wherein the frame is radially compressible and expandable between a radially compressed state and a radially expanded state;

wherein the frame comprises a plurality of actuators, each comprising first and second members that are axially moveable relative to each other to produce radial expansion and compression of the frame;

a plurality of leaflets situated within the frame, each leaflet comprising a body and two opposing commissure tabs arranged on opposite sides of the body; and a plurality of commissure attachment elements, wherein each commissure tab of a leaflet is paired with an adjacent commissure tab of an adjacent leaflet and the pair of commissure tabs are connected to one of the commissure attachment elements to form a plurality of commissures;

wherein each commissure attachment element is slidably mounted on the first member of one of the actuators such that the commissures can slide axially relative to the first members when the frame is radially expanded and compressed between the radially compressed state and the radially expanded state;

wherein each pivot joint comprises a pin coupling one of the first struts with one of the second struts and each commissure attachment element is retained by one of the pins; and an inner skirt connected to the frame, and each leaflet has a cusp edge portion stitched to the skirt along a scallop line having a plurality of peaks located at the pivot joints retaining the commissure attachment elements;

wherein the skirt has an outflow edge portion that is stitched to struts forming the pivot joints retaining the commissure attachment elements.

* * * * *